United States Patent
Nikoozadeh et al.

(10) Patent No.: US 11,446,003 B2
(45) Date of Patent: Sep. 20, 2022

(54) HIGH PERFORMANCE HANDHELD ULTRASOUND

(71) Applicant: Vave Health, Inc., Redwood City, CA (US)

(72) Inventors: Amin Nikoozadeh, San Carlos, CA (US); Jung Woo Choe, Sunnyvale, CA (US)

(73) Assignee: VAVE HEALTH, INC., Redwood City, CA (US)

( * ) Notice: Subject to any disclaimer, the term of this patent is extended or adjusted under 35 U.S.C. 154(b) by 1127 days.

(21) Appl. No.: 15/470,798

(22) Filed: Mar. 27, 2017

(65) Prior Publication Data

US 2018/0271483 A1 Sep. 27, 2018

(51) Int. Cl.
*A61B 8/00* (2006.01)
*A61B 8/08* (2006.01)
(Continued)

(52) U.S. Cl.
CPC .......... *A61B 8/4427* (2013.01); *A61B 8/4472* (2013.01); *A61B 8/5207* (2013.01);
(Continued)

(58) Field of Classification Search
CPC ..... A61B 8/0841; A61B 8/483; A61B 8/0883; A61B 8/488; A61B 8/5207; A61B 8/485;
(Continued)

(56) References Cited

U.S. PATENT DOCUMENTS

| 839,442 A | 12/1906 | Jesse |
| 4,413,629 A | 11/1983 | Durley, III |

(Continued)

FOREIGN PATENT DOCUMENTS

| CN | 1231835 A | 10/1999 |
| CN | 102525557 A | 7/2012 |

(Continued)

OTHER PUBLICATIONS

Ahn, et al. A new wireless hand-held ultrasound system with smartphone, tablet for mobile healthcare. 2015 IEEE International Ultrasonics Symposium Proceedings.
(Continued)

*Primary Examiner* — Baisakhi Roy
(74) *Attorney, Agent, or Firm* — Wilson Sonsini Goodrich & Rosati

(57) ABSTRACT

This disclosure generally relates to system design for a handheld ultrasound imaging system, which may generate an ultrasound image of tissue. The handheld ultrasound imaging system may comprise: an ultrasound transducer array to generate ultrasound waves comprising a wavelength; a processor coupled to the ultrasound transducer array, the processor configured with instructions that when executed cause the processor to: receive ultrasound data derived from the ultrasound transducer array and generate the plurality of ultrasound images, the plurality of ultrasound images comprising an axial resolution capable of resolving the tissue structure no more than the wavelength, and output the plurality of ultrasound images.

24 Claims, 18 Drawing Sheets

(51) Int. Cl.
*G01S 7/52* (2006.01)
*G01S 15/89* (2006.01)

(52) U.S. Cl.
CPC .............. *A61B 8/54* (2013.01); *A61B 8/565* (2013.01); *G01S 7/5208* (2013.01); *G01S 7/52026* (2013.01); *G01S 7/52082* (2013.01); *G01S 15/8915* (2013.01)

(58) Field of Classification Search
CPC ....... A61B 8/461; A61B 8/467; A61B 8/4427; A61B 8/4472; A61B 8/4477; A61B 8/565; H04N 19/184; H04N 19/96; H04N 19/98
See application file for complete search history.

(56) References Cited

U.S. PATENT DOCUMENTS

| | | |
|---|---|---|
| 4,589,284 A | 5/1986 | Breimesser et al. |
| 5,396,890 A | 3/1995 | Weng |
| 5,590,658 A | 1/1997 | Chiang et al. |
| 5,603,323 A | 2/1997 | Pflugrath et al. |
| 5,640,960 A | 6/1997 | Jones et al. |
| 5,778,177 A | 7/1998 | Azar |
| 5,795,297 A | 8/1998 | Daigle |
| 5,817,024 A | 10/1998 | Ogle et al. |
| 5,845,004 A | 12/1998 | Banjanin et al. |
| 5,851,186 A | 12/1998 | Wood et al. |
| 5,865,749 A | 2/1999 | Doten et al. |
| 5,891,030 A | 4/1999 | Johnson et al. |
| 5,944,659 A | 8/1999 | Flach et al. |
| 5,964,709 A | 10/1999 | Chiang et al. |
| 5,983,123 A | 11/1999 | Shmulewitz |
| 6,117,085 A | 9/2000 | Picatti et al. |
| 6,135,961 A | 10/2000 | Pflugrath et al. |
| 6,142,946 A | 11/2000 | Hwang et al. |
| 6,241,673 B1 | 6/2001 | Williams |
| 6,248,072 B1 | 6/2001 | Murkin |
| 6,248,073 B1 | 6/2001 | Gilbert et al. |
| 6,306,089 B1 | 10/2001 | Coleman et al. |
| 6,368,279 B1 | 4/2002 | Liu |
| 6,436,040 B1 | 8/2002 | Collamore et al. |
| 6,440,071 B1 | 8/2002 | Slayton et al. |
| 6,440,072 B1 | 8/2002 | Schuman et al. |
| 6,464,636 B1 | 10/2002 | Kinicki et al. |
| 6,471,651 B1 | 10/2002 | Hwang et al. |
| 6,530,887 B1 | 3/2003 | Gilbert et al. |
| 6,592,521 B1 | 7/2003 | Urbano et al. |
| 6,669,633 B2 | 12/2003 | Brodsky et al. |
| 6,755,789 B2 | 6/2004 | Stringer et al. |
| 6,780,154 B2 | 8/2004 | Hunt et al. |
| 6,783,493 B2 | 8/2004 | Chiang et al. |
| 6,969,352 B2 | 11/2005 | Chiang et al. |
| 7,022,075 B2 | 4/2006 | Grunwald et al. |
| 7,115,093 B2 | 10/2006 | Halmann et al. |
| 7,141,020 B2 | 11/2006 | Poland et al. |
| 7,199,738 B2 | 4/2007 | Han et al. |
| 7,223,242 B2 | 5/2007 | He et al. |
| 7,257,379 B2 | 8/2007 | Ozluturk et al. |
| 7,294,106 B2 | 11/2007 | Birkenbach et al. |
| 7,371,218 B2 | 5/2008 | Walston et al. |
| 7,394,410 B1* | 7/2008 | Wegener ................ H03M 7/30 341/50 |
| 7,458,935 B2 | 12/2008 | Cerofolini |
| 7,729,742 B2 | 6/2010 | Govari |
| 7,833,159 B2 | 11/2010 | Ahn et al. |
| D629,113 S | 12/2010 | Wodecki |
| 7,867,168 B2 | 1/2011 | Little et al. |
| 7,891,230 B2 | 2/2011 | Randall |
| D639,434 S | 6/2011 | Wodecki et al. |
| 7,984,651 B2 | 7/2011 | Randall et al. |
| 7,987,303 B2 | 7/2011 | Bartlett |
| 8,043,221 B2 | 10/2011 | Marteau et al. |
| 8,066,642 B1 | 11/2011 | Little et al. |
| 8,079,263 B2 | 12/2011 | Randall et al. |
| 8,488,013 B2 | 7/2013 | Jia et al. |
| 8,500,645 B2 | 8/2013 | Cohen et al. |
| 8,535,227 B2 | 9/2013 | Halmann et al. |
| 8,551,000 B2 | 10/2013 | Chiang et al. |
| 8,628,474 B2 | 1/2014 | Chiang et al. |
| 8,717,843 B2 | 5/2014 | Cerofolini |
| 8,852,103 B2 | 10/2014 | Rothberg et al. |
| 9,022,936 B2 | 5/2015 | Rothberg et al. |
| 9,028,412 B2 | 5/2015 | Rothberg et al. |
| 9,033,879 B2 | 5/2015 | Urness et al. |
| 9,033,884 B2 | 5/2015 | Rothberg et al. |
| 9,061,318 B2 | 6/2015 | Rothberg et al. |
| 9,067,779 B1 | 6/2015 | Rothberg et al. |
| 9,149,255 B2 | 10/2015 | Rothberg et al. |
| 9,151,832 B2 | 10/2015 | Little et al. |
| 9,155,521 B2 | 10/2015 | Rothberg et al. |
| 9,198,637 B2 | 12/2015 | Rothberg et al. |
| 9,229,097 B2 | 1/2016 | Rothberg et al. |
| 9,242,275 B2 | 1/2016 | Rothberg et al. |
| 9,247,924 B2 | 2/2016 | Rothberg et al. |
| 9,268,014 B2 | 2/2016 | Rothberg et al. |
| 9,268,015 B2 | 2/2016 | Rothberg et al. |
| 9,290,375 B2 | 3/2016 | Rothberg et al. |
| 9,327,142 B2 | 5/2016 | Rothberg et al. |
| 9,337,901 B2 | 5/2016 | Takahashi |
| 9,339,253 B2 | 5/2016 | Peszynski et al. |
| 9,351,706 B2 | 5/2016 | Rothberg et al. |
| 9,383,435 B2 | 7/2016 | Osawa |
| 9,392,996 B2 | 7/2016 | Chamberlain et al. |
| 9,394,162 B2 | 7/2016 | Rothberg et al. |
| 9,402,601 B1 | 8/2016 | Berger et al. |
| 9,476,969 B2 | 10/2016 | Rothberg et al. |
| 10,469,846 B2* | 11/2019 | Choe ................ H04N 19/96 |
| 10,681,357 B2* | 6/2020 | Choe ................ H04N 19/184 |
| 10,856,843 B2* | 12/2020 | Choe ................ G01S 15/8915 |
| 2002/0110196 A1 | 8/2002 | Nguyen et al. |
| 2002/0195910 A1 | 12/2002 | Hus et al. |
| 2002/0196465 A1* | 12/2002 | Ohta ................ H04N 1/00843 358/1.16 |
| 2003/0078501 A1 | 4/2003 | Barnes et al. |
| 2003/0080747 A1 | 5/2003 | Huelss |
| 2003/0097071 A1 | 5/2003 | Halmann et al. |
| 2003/0139664 A1 | 7/2003 | Hunt et al. |
| 2003/0139671 A1 | 7/2003 | Walston et al. |
| 2003/0167004 A1 | 9/2003 | Dines et al. |
| 2003/0181811 A1 | 9/2003 | Amemiya et al. |
| 2003/0187353 A1* | 10/2003 | Ng ................ G01S 7/52063 600/437 |
| 2004/0015079 A1 | 1/2004 | Berger et al. |
| 2004/0140965 A1* | 7/2004 | Wang ................ G06F 3/0321 345/179 |
| 2004/0225220 A1 | 11/2004 | Rich |
| 2006/0010296 A1 | 1/2006 | Dent |
| 2006/0058655 A1 | 3/2006 | Little |
| 2006/0072799 A1 | 4/2006 | McLain |
| 2006/0184042 A1* | 8/2006 | Wang ................ A61B 5/0095 600/476 |
| 2007/0016023 A1* | 1/2007 | Phelps ................ G01S 7/52046 600/437 |
| 2007/0242567 A1 | 10/2007 | Daft et al. |
| 2008/0114247 A1* | 5/2008 | Urbano ................ A61B 8/56 600/447 |
| 2008/0114248 A1 | 5/2008 | Urbano et al. |
| 2008/0114255 A1 | 5/2008 | Schwartz et al. |
| 2008/0137482 A1 | 6/2008 | Kang et al. |
| 2008/0208061 A1 | 8/2008 | Halmann |
| 2008/0214938 A1* | 9/2008 | Solomon ................ A61B 8/546 600/459 |
| 2008/0242992 A1 | 10/2008 | Criton |
| 2008/0262347 A1 | 10/2008 | Batchelder et al. |
| 2008/0285819 A1* | 11/2008 | Konofagou ............ A61B 8/485 382/128 |
| 2009/0177086 A1 | 7/2009 | Steen |
| 2010/0022822 A1 | 1/2010 | Walshe et al. |
| 2010/0022882 A1 | 1/2010 | Duckworth et al. |
| 2010/0027857 A1* | 2/2010 | Wang ................ A61B 5/4064 382/128 |
| 2010/0056956 A1 | 3/2010 | Dufresne et al. |

(56) References Cited

U.S. PATENT DOCUMENTS

| | | |
|---|---|---|
| 2010/0160786 A1 | 6/2010 | Nordgren et al. |
| 2010/0168576 A1* | 7/2010 | Poland ................ A61B 8/4427 600/443 |
| 2010/0249596 A1* | 9/2010 | Magee ................ G10K 11/346 600/447 |
| 2010/0268042 A1* | 10/2010 | Wang ................ G01N 29/2418 600/322 |
| 2010/0277305 A1 | 11/2010 | Garner et al. |
| 2010/0280315 A1* | 11/2010 | Pan ................ A61B 5/0066 600/109 |
| 2010/0280419 A1 | 11/2010 | Donskoy et al. |
| 2010/0305449 A1 | 12/2010 | Wegener et al. |
| 2011/0071397 A1 | 3/2011 | Wodnicki et al. |
| 2011/0245670 A1 | 10/2011 | Tashiro et al. |
| 2011/0286630 A1 | 11/2011 | Harder et al. |
| 2012/0013758 A1* | 1/2012 | Frederiksen ................ G06K 9/36 348/222.1 |
| 2012/0022379 A1 | 1/2012 | Gubbini et al. |
| 2012/0108975 A1 | 5/2012 | Marteau et al. |
| 2012/0265027 A1 | 10/2012 | Lee et al. |
| 2012/0289836 A1 | 11/2012 | Ukimura et al. |
| 2013/0023767 A1* | 1/2013 | Mammone ................ A61B 8/14 600/440 |
| 2013/0165796 A1 | 6/2013 | Tashiro |
| 2013/0184587 A1 | 7/2013 | Eom et al. |
| 2013/0226001 A1 | 8/2013 | Steen et al. |
| 2013/0229508 A1* | 9/2013 | Li ................ G06F 1/3287 348/77 |
| 2013/0261463 A1 | 10/2013 | Chiang et al. |
| 2013/0338498 A1* | 12/2013 | Emelianov ................ A61B 8/12 600/431 |
| 2013/0345566 A1 | 12/2013 | Weitzel et al. |
| 2014/0005547 A1 | 1/2014 | Balasubramanian |
| 2014/0024942 A1 | 1/2014 | Halmann et al. |
| 2014/0028479 A1 | 1/2014 | Cheung |
| 2014/0051984 A1 | 2/2014 | Berger et al. |
| 2014/0114190 A1 | 4/2014 | Chiang et al. |
| 2014/0121524 A1 | 5/2014 | Chiang et al. |
| 2014/0180097 A1 | 6/2014 | Rothberg et al. |
| 2014/0180100 A1 | 6/2014 | Rothberg et al. |
| 2014/0243614 A1 | 8/2014 | Rothberg et al. |
| 2014/0243669 A1 | 8/2014 | Halmann et al. |
| 2014/0275851 A1 | 9/2014 | Amble et al. |
| 2014/0288428 A1 | 9/2014 | Rothberg et al. |
| 2014/0300720 A1 | 10/2014 | Rothberg et al. |
| 2014/0357993 A1 | 12/2014 | Hiriyannaiah et al. |
| 2015/0032002 A1 | 1/2015 | Rothberg et al. |
| 2015/0038844 A1 | 2/2015 | Blalock et al. |
| 2015/0067441 A1 | 3/2015 | Gorissen et al. |
| 2015/0087987 A1 | 3/2015 | Ryu et al. |
| 2015/0092838 A1 | 4/2015 | Hiriyannaiah et al. |
| 2015/0160120 A1* | 6/2015 | Sun ................ G01N 29/2418 73/606 |
| 2015/0164477 A1 | 6/2015 | Ryu et al. |
| 2015/0208901 A1* | 7/2015 | Gazdzinski ................ A61B 8/12 600/302 |
| 2015/0216509 A1 | 8/2015 | Yamagata et al. |
| 2015/0245823 A1 | 9/2015 | Jin et al. |
| 2015/0247921 A1 | 9/2015 | Rothberg et al. |
| 2015/0250454 A1 | 9/2015 | Lee |
| 2015/0297192 A1 | 10/2015 | Chamberlain et al. |
| 2015/0297193 A1 | 10/2015 | Rothberg et al. |
| 2015/0325036 A1 | 11/2015 | Lee |
| 2015/0326872 A1 | 11/2015 | Lee et al. |
| 2015/0366538 A1 | 12/2015 | Mckenna |
| 2015/0381995 A1* | 12/2015 | Han ................ H04N 9/64 382/166 |
| 2016/0007957 A1 | 1/2016 | Murphy et al. |
| 2016/0008556 A1* | 1/2016 | Baym ................ A61M 5/427 604/506 |
| 2016/0009544 A1 | 1/2016 | Rothberg et al. |
| 2016/0015368 A1 | 1/2016 | Poland |
| 2016/0069989 A1 | 3/2016 | Rothberg et al. |
| 2016/0100824 A1 | 4/2016 | Kim |
| 2016/0120507 A1 | 5/2016 | Ninomiya et al. |
| 2016/0125641 A1 | 5/2016 | Lee et al. |
| 2016/0131748 A1 | 5/2016 | Little et al. |
| 2016/0151045 A1 | 6/2016 | Pelissier et al. |
| 2016/0199036 A1 | 7/2016 | Pelissier et al. |
| 2016/0202349 A1 | 7/2016 | Rothberg et al. |
| 2016/0207760 A1 | 7/2016 | Rothberg et al. |
| 2016/0228091 A1 | 8/2016 | Chiang et al. |
| 2016/0228092 A1 | 8/2016 | Kim et al. |
| 2016/0270764 A1* | 9/2016 | Wodecki ................ A61B 8/4405 |
| 2016/0280538 A1 | 9/2016 | Rothberg et al. |
| 2016/0290969 A1 | 10/2016 | Rothberg et al. |
| 2016/0290970 A1 | 10/2016 | Rothberg et al. |
| 2016/0338676 A1 | 11/2016 | Berger et al. |
| 2016/0345936 A1 | 12/2016 | Cho et al. |
| 2016/0377717 A1* | 12/2016 | Srinivasan ................ G01S 7/52034 367/7 |
| 2017/0000457 A1 | 1/2017 | Chamberlain et al. |
| 2017/0027547 A1 | 2/2017 | Haugaard et al. |
| 2017/0029271 A1 | 2/2017 | Rothberg et al. |
| 2017/0067988 A1 | 3/2017 | Rothberg et al. |
| 2017/0143313 A1 | 5/2017 | Pelissier et al. |
| 2017/0238907 A1 | 8/2017 | Kommu CHS |
| 2018/0008233 A1* | 1/2018 | Pelissier ................ G01S 15/892 |
| 2018/0271482 A1 | 9/2018 | Choe et al. |
| 2018/0271483 A1 | 9/2018 | Nikoozadeh et al. |
| 2019/0069884 A1* | 3/2019 | Dickie ................ A61B 8/14 |
| 2019/0349758 A1* | 11/2019 | Zhu ................ H04W 12/50 |
| 2021/0113186 A1* | 4/2021 | Choe ................ A61B 8/4427 |

FOREIGN PATENT DOCUMENTS

| | | |
|---|---|---|
| CN | 103284735 A | 9/2013 |
| EP | 2135110 A2 | 12/2009 |
| EP | 2863805 A1 | 4/2015 |
| JP | S5215372 A | 2/1977 |
| JP | 2002530142 A | 9/2002 |
| JP | 2003033350 A | 2/2003 |
| JP | 2012120691 A | 6/2012 |
| JP | 2013158589 A | 8/2013 |
| WO | WO-9701768 A2 | 1/1997 |
| WO | WO-0030540 A1 | 6/2000 |
| WO | WO-0066001 A1 | 11/2000 |
| WO | WO-0079300 A1 | 12/2000 |
| WO | WO-03069761 A1 | 8/2003 |
| WO | WO-2008124841 A2 | 10/2008 |
| WO | WO-2008146201 A2 | 12/2008 |
| WO | WO-2009135255 A1 | 11/2009 |
| WO | WO-2013148730 A2 | 10/2013 |
| WO | WO-2013162244 A1 | 10/2013 |
| WO | WO-2014003404 A1 | 1/2014 |
| WO | WO-2014123922 A1 | 8/2014 |
| WO | WO-2014134175 A2 | 9/2014 |
| WO | WO-2014151362 A2 | 9/2014 |
| WO | WO-2014151525 A2 | 9/2014 |
| WO | WO-2014165662 A2 | 10/2014 |
| WO | WO-2015013245 A2 | 1/2015 |
| WO | WO-2015048327 A2 | 4/2015 |
| WO | WO-2015161147 A1 | 10/2015 |
| WO | WO-2015161157 A1 | 10/2015 |
| WO | WO-2015161164 A1 | 10/2015 |
| WO | WO-2015161292 A1 | 10/2015 |
| WO | WO-2016011000 A1 | 1/2016 |
| WO | WO-2016052817 A1 | 4/2016 |
| WO | WO-2016057622 A1 | 4/2016 |
| WO | WO-2016057631 A1 | 4/2016 |
| WO | WO-2017013443 A1 | 1/2017 |

OTHER PUBLICATIONS

Ahn, et al. Smartphone-based portable ultrasound imaging system: Prototype implementation and evaluation. Conference: Oct. 2015 IEEE International Ultrasonics Symposium (IUS). DOI: 10.1109/ULTSYM.2015.0517.

Almekkawy, et al. An optimized ultrasound digital beamformer with dynamic focusing implemented on FPGA. Conf Proc IEEE Eng

(56) References Cited

OTHER PUBLICATIONS

Med Biol Soc. 2014;2014:3296-9. doi: 10.1109/EMBC.2014.6944327.

Daft, et al. Matrix Transducer Design with Improved Image Quality and Acquisition Rate. Conference: Ultrasonics Symposium, Nov. 2007, IEEE. DOI: 10.1109/ULTSYM.2007.112.

Fuller, et al. Real time imaging with the Sonic Window: A pocket-sized, C-scan, medical ultrasound device. Conference: Ultrasonics Symposium (IUS), Oct. 2009 IEEE International. DOI: 10.1109/ULTSYM.2009.5441943.

Hewener, et al. Mobile ultrafast ultrasound imaging system based on smartphone and tablet devices. Ultrasonics Symposium (IUS), Oct. 2015 IEEE International.

Hoegh, et al. Ultrasonic Tomography for Evaluation of Concrete Pavements. Transportation Research Record: Journal of the Transportation Research Board. 2011. vol. 2232. DOI: 10.3141/2232-09.

Hwang, et al. Portable ultrasound device for battlefield trauma. Conference: Ultrasonics Symposium, 1998. Proceedings, Feb. 1998 IEEE, vol. 2. DOI: 10.1109/ULTSYM.1998.765266.

Kim, et al. A new nonlinear zone-based beamforming method for point-of-care ultrasound: Algorithms and implementation. 2014 IEEE International Ultrasonics Symposium pp. 2137-2140.

Kim, et al. A single FPGA-based portable ultrasound imaging system for point-of-care applications. IEEE Trans Ultrason Ferroelectr Freq Control. Jul. 2012;59(7):1386-94. doi: 10.1109/TUFFC.2012.2339.

Nippon Pulse America, Inc. S040 Linear Shaft Motor for Small-Scale High Precision. Web article. Aug. 9, 2011. URL:<http://www.nipponpulse.com/news/view/s040-linear-shaft-motor-for-small-scale-high-precision>.

Ruiter, et al. First results of a clinical study with 3D ultrasound computer tomography. Ultrasonics Symposium (IUS), 2013 IEEE International.

Yang, et al. A Comparison of the Lookup Table and On-The-Fly Calculation Methods for the Beamforming Control Unit. ITC-CSCC : 2008, Jul. 2008, 657-660 (4 pages).

European Application No. 18771485.2 Search Report dated Nov. 23, 2020.

PCT/US2018/024059 International Patent Report on Patentability dated Oct. 3, 2019.

PCT/US2018/024059 International Search Report and Written Opinion dated Aug. 9, 2018.

U.S. Appl. No. 15/470,700 Non-Final Office Action dated May 1, 2020.

U.S. Appl. No. 16/576,288 Non-Final Office Action dated Jan. 17, 2020.

* cited by examiner

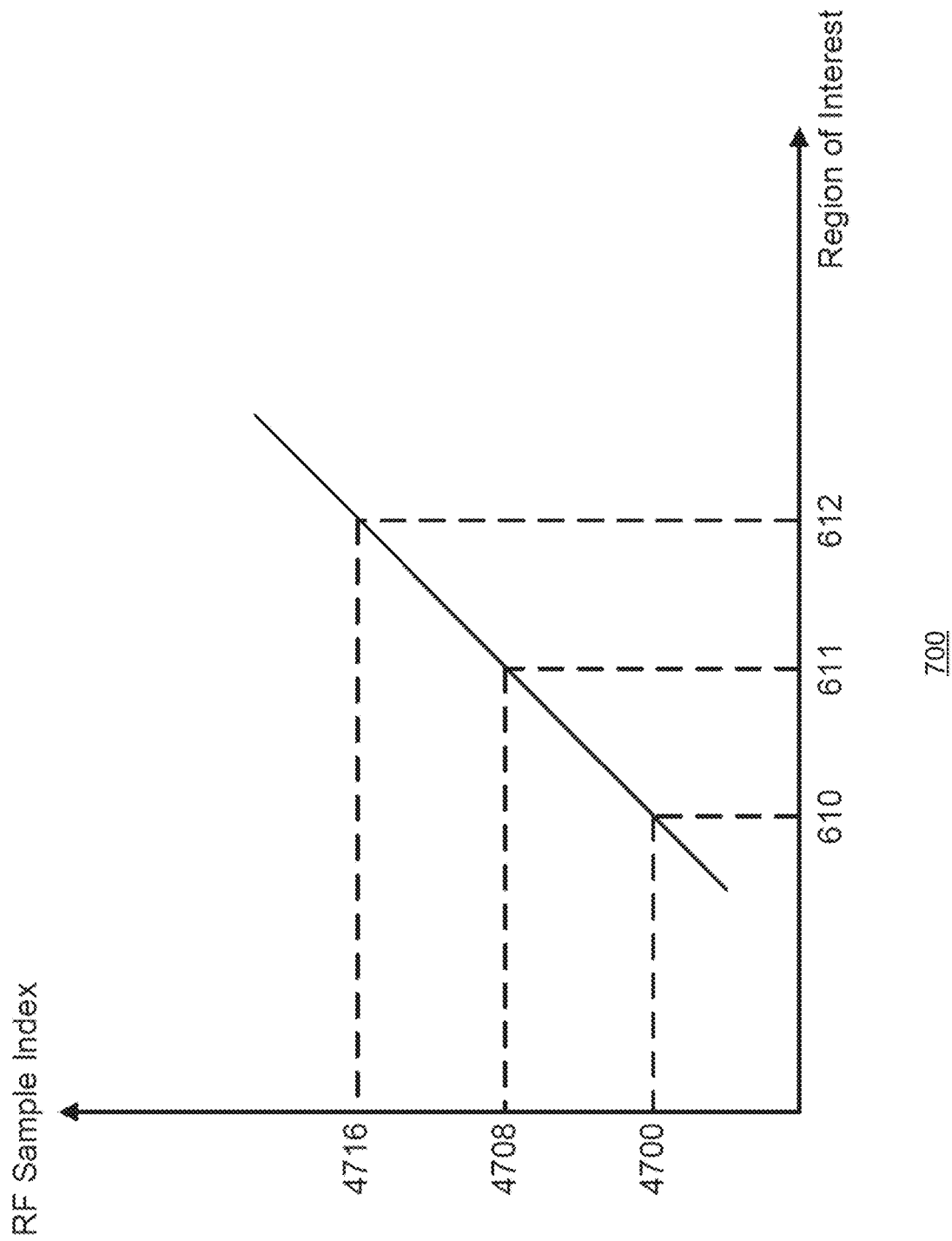

| Region of Interest | ... | 610 | 611 | 612 | 613 | 614 ... |
|---|---|---|---|---|---|---|
| Memory Contents (Delay Times) | ... | 4700 | 4708 | 4716 | 4724 | 4732 ... |

| Memory Address (RF Sample Indices) | ... | 4699 | 4700 | 4701 | ... | 4707 | 4708 | 4709 | ... | 4715 | 4716 | 4717 |
|---|---|---|---|---|---|---|---|---|---|---|---|---|
| Memory Contents (Flags) | ... | 0 | 1 | 0 | ... | 0 | 1 | 0 | ... | 0 | 1 | 0 |

NZ (7 Zeros) NZ (7 Zeros)

HIGH PERFORMANCE HANDHELD ULTRASOUND

BACKGROUND

Prior methods and apparatus to generate ultrasound image data with a handheld imaging system can be less than ideal in at least some respects. The prior handheld ultrasound imaging systems may have less than ideal image resolution, which can decrease clinical utility. For example, small image detail which can be relevant to the diagnosis and treatment of patients may not be present in images of at least some of the prior ultrasound systems with handheld probes. The prior ultrasound imaging systems have greater complexity than would be ideal, which can increase the cost, weight, power consumption, and size of a handheld ultrasound probe. With real-time ultrasound imaging, latencies can result in a less than ideal performance. For example, a user will often align the probe with a target tissue and delays in showing images on the display can make alignment of the probe with a moving target tissue more difficult than would be ideal. For other real-time applications such as robotic surgery and telemedicine, latencies in generating images can also result in less than ideal system performance and the decrease responsiveness of the system. The amount of bandwidth required to reliably transmit data wirelessly with prior systems can be greater than would be ideal, which can result in additional degradation and latencies of transmitted ultrasound data. Prior handheld imaging systems can weigh more than would be ideal.

In light of the above, improved methods and apparatus for generating ultrasound images with a handheld ultrasound imaging system would be helpful. Ideally, such improved methods and apparatus would provide ultrasound images with increased image resolution and faster data transmission with decreased data size for each image, decreased latencies, complexity, power consumption and probe weight.

SUMMARY

The systems and methods disclosed herein provide improved imaging with a handheld (or "hand held") ultrasound imaging system. The probe is configured to generate images capable of spatially resolving tissue structures no more than a wavelength of ultrasound waves emitted from the handheld ultrasound imaging system. The spatial resolution of the tissue structure may comprise an axial resolution of the image along the ultrasound beam path. The handheld ultrasound imaging system comprises an ultrasound transducer array and a processor configured to generate pixels of the images and can be configured to generate compressed images that resolve the tissue structure. The ultrasound imaging system can be configured to compress individual pixels of the images and provide images comprising the compressed pixels, such that the compressed images comprise the spatial resolution of the uncompressed images. The ultrasound imaging system may comprise communication circuitry to transmit compressed image data such as compressed pixels of the ultrasound images. The communication circuitry may be wireless or wired, or combinations thereof. The communication circuitry and processor can be configured such that the communication circuitry transmits first pixels of an image from the handheld ultrasound imaging system prior to receiving last pixels of an image from the processor in order to decrease latencies, which can be helpful with transmission over networks such as wireless networks. The handheld ultrasound imaging system may comprise an analog-to-digital (A/D) converter coupled to the transducer array and the processor. The ultrasound imaging system may comprise a housing to support the ultrasound transducer array, the A/D converter, the processor and the communication circuitry. The handheld ultrasound imaging system may comprise a weight of no more than 300 grams (g) and draw power of no more than about 15 watts (W) when performing real-time imaging of the tissue with a resolution capable of resolving the tissue structure displayed in the image.

The handheld ultrasound system comprises a plurality of components arranged to provide a decreased size and weight. In some instances, the handheld ultrasound system is configured to be held in the hand of a user. In some cases, the handheld ultrasound system is configured to allow a patient to conduct a measurement on himself or herself. The handheld ultrasound system comprises a housing to contain the measurement components, and the housing is sized, in some instances, such that the user can readily grasp the housing and lift the measurement components within the housing. The compactness and decreased mass of the handheld ultrasound system allows the system to be easily held in the hand and transported. In many embodiments, the probe of the handheld ultrasound system comprises a maximum dimension across within a range from about 80 mm to about 200 mm, or about 100 mm to about 140 mm, or about 110 mm to about 130 mm, and a mass within a range from about 100 grams to about 500 grams, or about 200 grams to about 400 grams, or about 250 grams to about 350 grams. In many embodiments, the handheld ultrasound system is configured without internal moving parts in order to increase the reliability of the system. The handheld ultrasound system is optionally configured to be dropped from a distance of about one foot, and provide a change in measurement repeatability and accuracy of no more than 1%, for example.

In a first aspect, a handheld ultrasound probe for generating a plurality of ultrasound images of tissue structure comprises an ultrasound transducer array to generate ultrasound waves comprising a wavelength. A processor is coupled to the ultrasound transducer array. The processor is configured with instructions that when executed cause the processor to receive ultrasound data derived from the ultrasound transducer array and generate the plurality of ultrasound images, the plurality of ultrasound images comprising an axial resolution capable of resolving the tissue structure no more than the wavelength. The processor is configured with instructions to output the plurality of ultrasound images.

In another aspect, a method for generating a plurality of ultrasound images of tissue structure with a handheld ultrasound imaging probe comprises generating ultrasound waves with an ultrasound transducer array, in which the ultrasound waves comprise a wavelength. Ultrasound data from the ultrasound transducer array is received with an A/D converter. The plurality of ultrasound images are generated with a processor, in which the plurality of ultrasound images comprise an axial resolution resolving the tissue structure no more than the wavelength. The plurality of ultrasound images is output from the handheld ultrasound imaging probe.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "Figure" and "FIG." herein), of which:

FIG. 7 shows a simplified graph of a portion of a delay curve associated with the time delays for receipt of an ultrasound signal from each location in a line, for one transducer channel.

FIG. 8A shows a simplified example delay table for a channel in an example ultrasound transducer array.

FIG. 8B shows a simplified flag table for a channel in an example ultrasound transducer array.

DETAILED DESCRIPTION

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

In the figures shown herein, like numbers refer to like elements.

Figure 1:
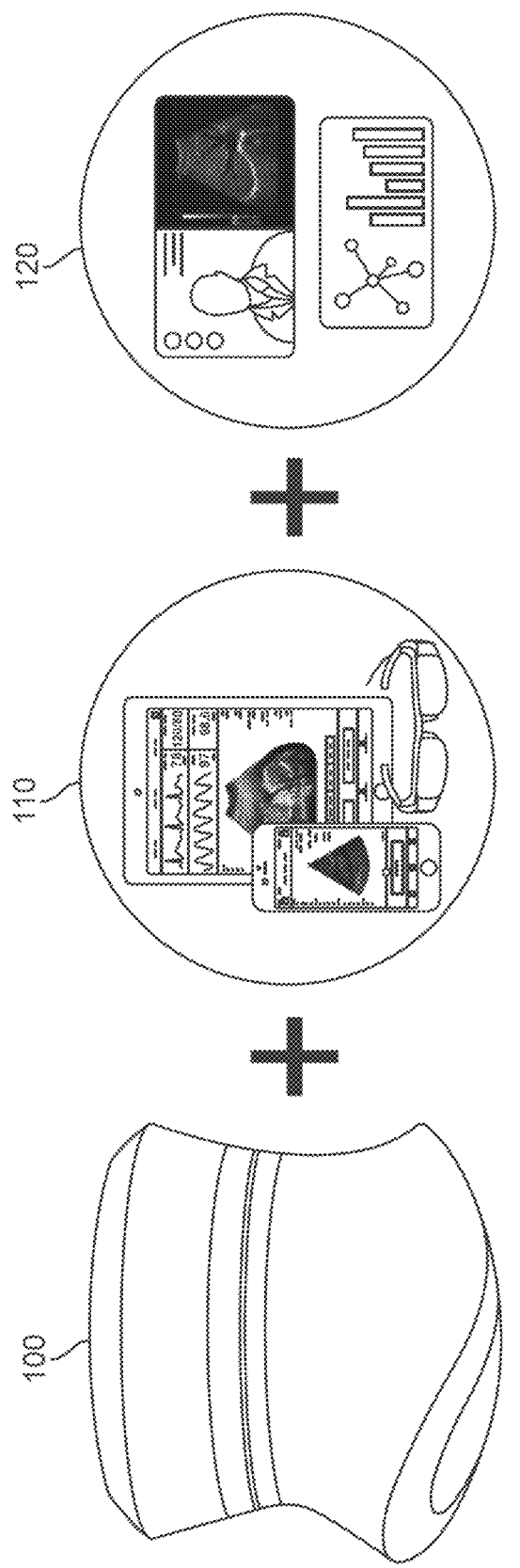
FIG. 1 illustrates a schematic of a handheld ultrasound system capable of communicating with an external device.

FIG. 1 illustrates a schematic of a handheld ultrasound system capable of communicating with an external device. The handheld ultrasound device 100 may comprise one or more ultrasonic transducer arrays (each comprising one or more ultrasonic transducers), one or more ultrasound beamforming components, one or more electronic devices to control the beamforming components, one or more batteries or external power modules, and one or more wireless transceivers.

The handheld ultrasound device can utilize components that are selected and arranged in such a manner as to provide a decreased size and weight. The handheld ultrasound device can be configured to be held in the hand of a user. The handheld ultrasound device can be configured to allow a patient to conduct a measurement on himself or herself. The handheld ultrasound device can comprise a housing to contain the measurement components, and the housing can be sized such that the user can readily grasp the housing and lift the measurement components within the housing. The compactness and decreased mass of the handheld ultrasound device can allow the system to be easily held in the hand and transported.

The probe of the handheld ultrasound device can comprise a maximum dimension across within a range from about 80 mm to about 200 mm, about 100 mm to about 180 mm, about 100 mm to about 140 mm, about 120 mm to about 160 mm, about 110 mm to about 130 mm, or about 130 mm to about 150 mm, for example. The probe of the handheld ultrasound device can comprise a second shorter dimension across within a range from about 10 mm to about 90 mm, about 20 mm to about 80 mm, about 30 mm to about 70 mm, or about 40 mm to about 60 mm. The probe of the handheld ultrasound device may comprise a third dimension across within a range from about 5 mm to about 45 mm, about 10 mm to about 40 mm, about 15 mm to about 35 mm, or about 20 mm to about 30 mm, for example. The probe of the handheld ultrasound device can comprise a mass within a range from about 100 grams to about 500 grams, about 200 grams to about 400 grams, or about 250 grams to about 350 grams.

The handheld ultrasound device can be configured without internal moving parts in order to increase the reliability of the system. The handheld ultrasound device can be optionally configured to be dropped from a distance of about one foot, and provide a change in measurement repeatability and accuracy of no more than 1%, for example.

The handheld ultrasound device can utilize components selected and arranged in such a manner as to require and/or consume less memory and power as compared with conventional or non-handheld ultrasound devices. One or more of the ultrasound beamforming components can be implemented on a field programmable gate array (FPGA). In some instances, all of the beamforming components are implemented on the FPGA. One or more of the ultrasound beamforming components can be implemented on an application specific integrated circuit (ASIC). In some instances, all of the beamforming components are implemented on the ASIC.

The FPGA or ASIC can utilize an equivalent gate count of no more than about 1,000,000 gates, no more than about 500,000 gates, no more than about 200,000 gates, no more than about 100,000 gates, no more than about 50,000 gates, no more than about 20,000 gates, or no more than about 10,000 gates. The FPGA or ASIC can utilize an equivalent gate count within a range defined by any two of the preceding values. The FPGA or ASIC can utilize memory resources of no more than about 10,000 kilobits, no more than about 5,000 kilobits, no more than about 2,000 kilobits, no more than about 1,000 kilobits, no more than about 500 kilobits, no more than about 200 kilobits, or no more than about 100 kilobits. The FPGA or ASIC can utilize memory resources within a range defined by any two of the preceding values. The FPGA or ASIC can have a power draw of no more than about 1000 mW, no more than about 500 mW, no more than about 200 mW, no more than about 100 mW, no more than about 50 mW, no more than about 20 mW, or no more than about 10 mW. The FPGA or ASIC can have a power draw within a range defined by any two of the preceding values.

One or more energy storage units (e.g., batteries or external power modules) can be used to power the handheld ultrasound device. The energy storage units can allow the handheld ultrasound device to be utilized for a lifetime of greater than about 0.5 hours, greater than about 1 hour, greater than about 2 hours, greater than about 5 hours, or greater than about 10 hours when the handheld ultrasound device is in continuous operation. The batteries or external power modules can allow the handheld ultrasound device to be utilized for a lifetime within a range defined by any two of the preceding values.

The handheld ultrasound device can be configured to utilize the systems and methods described herein to operate with reduced memory and computational processing requirements as compared to traditional, non-handheld ultrasound devices. The handheld ultrasound device can be configured to utilize a memory no greater than 68 kB for a 32 channel ultrasound system utilizing the systems and methods described herein. The handheld ultrasound device can be configured to utilize a memory no greater than 2.5 kB per channel of the ultrasound system. The Rx beamformer can be configured to utilize a memory no greater than 68 kB for a 32 channel ultrasound system. The Rx beamformer can be configured to utilize a memory no greater than 2.5 kB per channel of the ultrasound system.

The systems and methods described herein can allow reduced memory and computational processing requirements while maintaining high-quality ultrasound imaging capabilities. In particular, the systems and methods can allow the ultrasound beamforming operations with minimal error in calculated delay times. The systems and methods described herein can allow operations with errors in delay times that are within half of an RF sampling period.

The systems and methods described herein may allow reduced memory, computational, and communication processing requirements while maintaining high-quality ultrasound imaging capabilities. In particular, the systems and methods may allow a plurality of ultrasound images to be compressed, thereby yielding one or more advantages, such as (i) a reduction in memory requirements, (ii) a reduction in the amount of data transferred from the portable ultrasonic device to the display (e.g., over a wireless communication), and (iii) an increased sensitivity of low-intensity signals made possible by compression with a non-linear function.

The handheld ultrasound device may communicate the results of an ultrasound measurement via a wireless communication channel to a portable electronic device 110 (such as a tablet, smartphone, smartwatch, smartglasses, or other portable electronic device), a desktop monitor or laptop display (e.g., a liquid crystal display (LCD)), or a television (e.g, a flat panel TV or a smart TV). The handheld ultrasound device can communicate the results of an ultrasound measurement via a communication channel (e.g., wireless or wired) to a television or computer monitor. The wireless communication circuitry may be via Bluetooth communication or other short distance wireless communication. The wireless communication may be via any other wireless communication known to one having skill in the art.

The results may be partially or fully processed ultrasound images. All processing of the ultrasound image may be performed on the handheld ultrasound device. For instance, the handheld ultrasound device may include hardware or software elements that allow ultrasound signals to be converted into electronic representations. The handheld ultrasound device may further include hardware or software elements that allow processing of the electronic representations to extract, for instance, an ultrasound image. The handheld ultrasound device can further include hardware or software elements that allow post-processing of the ultrasound image to improve the image quality.

The handheld electronic device may display results and analysis of the ultrasound measurement on one or more mobile applications 120. Alternatively or in combination, the portable electronic device may display results and analysis of the ultrasound measurement on one or more desktop monitor, laptop displays, or television displays. The applications may comprise mobile applications, desktop applications, laptop application, or television applications. The one or more mobile applications may comprise an environment that displays the ultrasound image. The one or more mobile applications may comprise an environment that allows sharing of the ultrasound image with a specialist, such as a radiologist or ultrasound technician. The specialist may interpret the results of the ultrasound image to provide clinical advice, such as a diagnosis, based on the results of the ultrasound image. In this manner, the handheld ultrasound system may be used by a patient or by a health care provider even in facilities lacking access to specialists capable of interpreting ultrasound results. The one or more applications may allow sharing of ultrasound images with a specialist in near real time. This capability may allow the specialist to provide instructions to the user on how to operate the handheld ultrasound device. For instance, the near real-time image sharing capability may allow the specialist to direct a patient or health care provider to move the handheld ultrasound device to a different location on the patient's body. The real-time image sharing capability may provide near real-time feedback on whether the handheld ultrasound is properly positioned to obtain ultrasound images of a desired location within the patient's body. In this manner, the handheld ultrasound system may be used even by a patient or health care provider who has little or no experience in the use of ultrasound systems.

Figure 2:
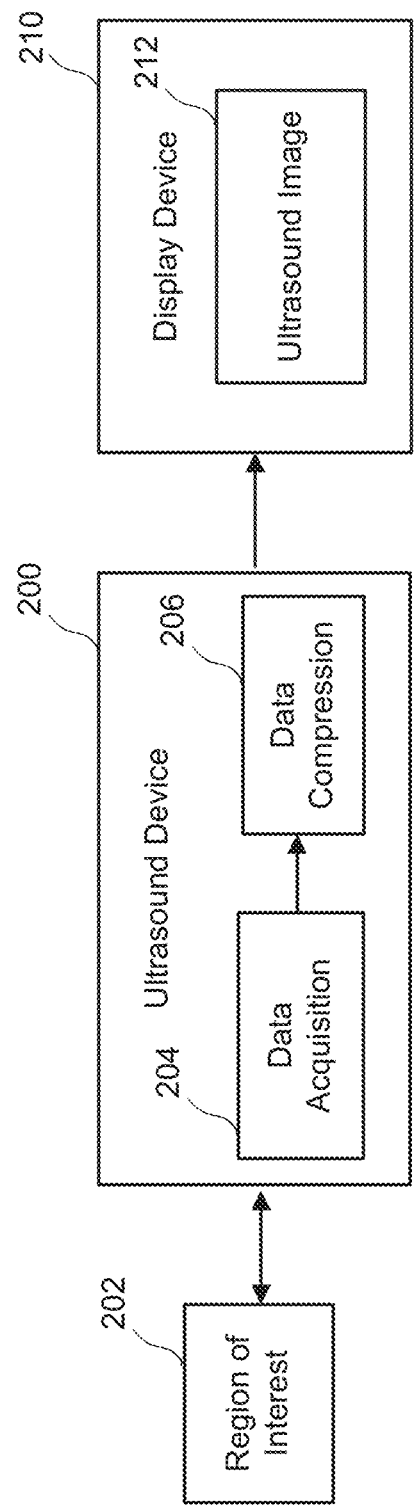
FIG. 2 illustrates a block diagram of an ultrasound imaging device used to image a region of interest.

FIG. 2 illustrates a block diagram of an ultrasound imaging device used to image a region of interest. An ultrasound device 200 sends ultrasonic energy, such as in the form of ultrasonic waves, to a medium based on a particular region of interest 202, and receives reflected ultrasonic waves from the region of interest. The region of interest may comprise a space that is being imaged. The region of interest may include any one or more objects. The region of interest may comprise a region inside of a patient's body. In some cases, the region of interest may comprise a fetus in a womb. In some instances, the region of interest may comprise an internal organ of the patient, such as a heart, lung, kidney, bladder, or any other organ. The region of interest may comprise a portion of an organ. The region of interest may comprise more than one organ. In some cases, the region of interest may comprise multiple objects clustered in the same vicinity. For example, the region of interest may include a cluster of objects such as multiple bladder stones in a bladder. In some cases, the region of interest may represent multiple portions or landmarks of an organ, such as multiple components of a heart. For example, such portions or landmarks of a heart may include a right ventricle, a left ventricle, a right atrium, a left atrium, and a thoracic aorta. The systems and methods described herein may be applied to imaging of regions that include multiple objects.

As described in more detail below, the ultrasound device 200 processes the reflected ultrasonic waves and sends processed image data to a display device 210. The ultrasound device 200 is configured to process data as described herein. The ultrasound device comprises data acquisition circuitry 204, and data compression circuitry 206 to compress data received from the data acquisition circuitry.

The display device displays an ultrasound image 212 based on the processed image data received from the ultrasound device. In some cases, the ultrasound image shows one or more objects located in a particular space that reflect ultrasonic waves emitted by the ultrasound device back to the ultrasound device. The display device may be located at a position near to the ultrasound device, such as in the same room as the ultrasound device. The display device may be located at a position remote from the ultrasound device. For instance, the ultrasound device may be located at a physician's office while the display device is located at a hospital or the office of a specialist who is able to interpret ultrasound images. The display device may be configured to communicate with an image reproduction device such as a digital display, a printer, a wearable device, an augmented-reality device, a virtual-reality device, a 3-dimensional (3D) display, etc.

Although reference is made to circuitry to acquire and compress ultrasound data, the data acquisition and data compression circuitry as described herein can be configured in many ways to process and compress many types of data, and the type of data acquired and compressed is not limited to ultrasound data. Further the data acquisition and compression circuitry as described herein can be located off of a handheld probe. Data acquisition circuitry 204 can be configured to acquire data from any data source, such as a video signal, an audio signal, an ultrasound or other medical imaging signal, a sound wave, an electrical signal, or another type of analog or digital signal, for example. Data compression circuitry 206 can be configured to compress the acquired data with any type of data compression method such as image compression or pixel compression as described herein, for example. Alternatively or in combination, data compression circuitry 206 can be configured to compresses analog or digital data and may produce analog or digital compressed data. Image compression may be performed by a lossless or lossy compression method (e.g. JPEG, GIF). Pixel compression may be performed by reducing the number of bits representing a pixel, such as dynamic range reduction using a lookup table (e.g., using a compression function), bit truncation (e.g., removing one or more most significant bits or least significant bits), or averaging adjacent pixel values. The data compression circuitry 206 may be configured to downsample of images (e.g., removing a portion of images from the data to reduce frame rate) or pixels (e.g., removing a portion of pixels from the data to reduce spatial resolution of images).

Figure 3:
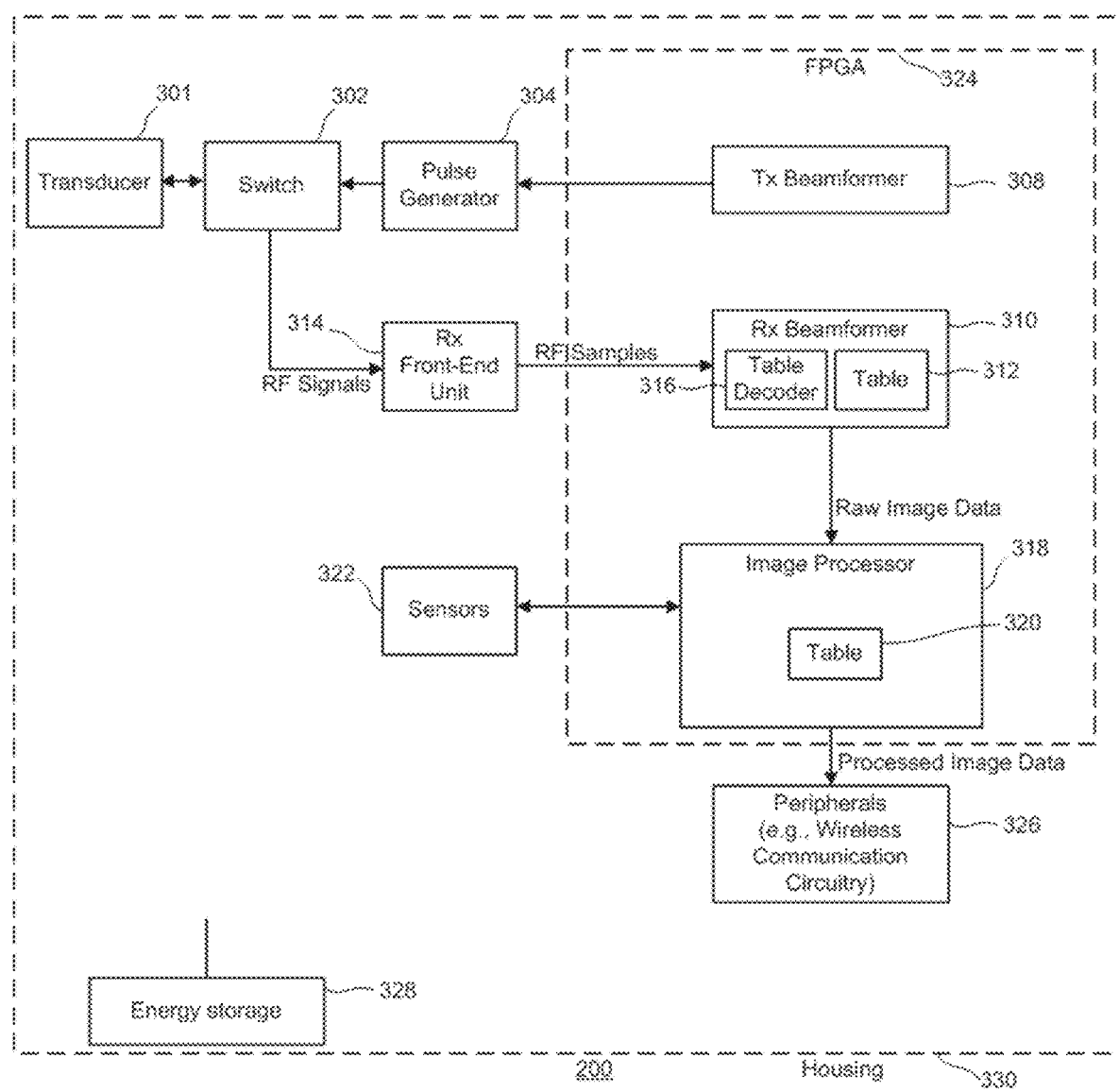
FIG. 3 illustrates a block diagram of an example ultrasound imaging device, which may be used for some embodiments described herein.

FIG. 3 illustrates a block diagram of an example ultrasound device 200, which may be used for some implementations described herein. For example, ultrasound device 200 may be used to implement ultrasound device 100 of FIG. 1. In some implementations, ultrasound device 200 includes a transducer array 301, a switch 302, and a pulse generator 304. Transducer array 301 may also be referred to as transducer 301. Ultrasound device 200 may include a transmit (Tx) beamformer 308 and/or a receive (Rx) beamformer 310. Rx beamformer 310 may include a memory that stores a table 312. Ultrasound device 200 may include an Rx front-end unit 314 and/or an image processor 318. In some implementations, ultrasound device 200 also includes sensors 322 and/or peripherals 326.

In some implementations, a table 312 may be stored on FPGA 324, or stored on any other suitable storage device. Furthermore, in various implementations, FPGA 324 may not have all of the components shown and/or may have other elements including other types of elements instead of, or in addition to, those shown herein. For example, in some implementations, FPGA 324 may include image processor 318. Furthermore, while image processor 318 is described herein as performing separate functions, in some implementations, a single processing unit such as FPGA 324 may perform all of the functions and implementations described herein.

For ease of illustration, FIG. 3 shows one block for each of component of ultrasound device 200. In other implementations, ultrasound device 200 may not have all of the components shown and/or may have other elements including other types of elements instead of, or in addition to, those shown herein.

In operation, Tx beamformer 308 causes pulse generator 304 to generate electrical signals based on transmit beamforming, where the electrical signals are applied to transducer array (or "transducer") 301. The electrical signals or pulses may be produced at a predetermined pulse rate (e.g., 1,000 pulses per second, etc.), depending on the particular implementation. For instance, the electrical signals can be produced at a rate greater than 100 pulses per second, greater than 200 pulses per second, greater than 500 pulses per second, greater than 1000 pulses per second, greater than 2000 pulses per second, greater than 5000 pulses per second, or greater than 10000 pulses per second. The electrical signals may be produced at a pulse rate within a range defined by any two of the preceding values. The pulse generator may control the length of a pulse. The pulse generator may control the total number of pulses applied during a signal acquisition. The pulse generator may control the amplitude of the electrical signals, which may in turn control the intensity and energy of an ultrasound beam produced by the transducer array.

The switch 302 selects one of two operating modes: (1) select the signal in the direction from the pulse generator 304 to the transducer 301 or (2) select the signal in the direction from the transducer 301 to the Rx front-end unit 314.

In various implementations, pulse generator 304 controls the amplitude of the electrical signals or pulses, which in turn controls the intensity and energy of an ultrasound beam produced by transducer array 301, after the signal is selected in the direction from the pulse generator 304 to the transducer array 301 by the switch 302. Pulse generator 304 may also control the width of the pulses (which in turn controls the signal frequency) and the number of cycles in the pulses (which in turn controls the energy and the bandwidth of the signal).

Transducer array 301 generates ultrasonic waves based on the electrical signals received from pulse generator 304. The ultrasonic waves may also be referred to as ultrasound waves, ultrasonic pulses, or ultrasound pulses.

In various implementations, transducer array 301, also referred to as a transducer or probe, is positioned in direct contact with a surface such as the body of a patient (e.g., the abdomen of a patient). In some implementations, the probe need not be in direct contact with the surface. For example, there may be water or another medium between the probe and the surface. In some implementations, when the probe is in direct contact with the surface, an ultrasound gel may be used to couple the probe with the surface. Transducer array 301 focuses a beam of ultrasonic waves or pulses to give the beam a particular size and shape at various depths within a particular space/area beneath the surface (e.g., a portion of patient's body). Transducer array 301 also scans the beam over the space that is being imaged (e.g., over an anatomical area). The space that is being imaged may also be referred to as a region of interest.

In various implementations, transducer array 301 includes one or more transducer elements. Each transducer element can be referred to as a channel. The transducer array can comprise 32 transducer elements, 64 transducer elements, 128 transducer elements, or 256 transducer elements. The transducer array can comprise a number of elements within a range defined by any two of the preceding values. The transducer array can comprise fewer than 64 or fewer than 32 transducer elements. The transducer array can comprise more than 256 transducer elements.

In some cases, each of the transducer elements can be of the same type. For example, the transducer elements can be piezoelectric transducer elements. The transducer elements can be capacitive transducer elements. The transducer elements can be any transducer element as is known to one having skill in the art. In some cases, the transducer elements can vary in type. For instance, some transducer elements can be piezoelectric transducer elements while other transducer elements are capacitive transducer elements. When an electrical pulse is applied to a given transducer element, the transducer element vibrates and produces the ultrasound, or ultrasonic wave, which is directed at the region of interest. Conversely, when a given transducer element is vibrated by returning ultrasound echoes from objects in the region of interest, the transducer element produces radio frequency (RF) signals. Since the transducer elements can act to both produce and receive ultrasound signals, the ultrasound device can further comprise a switch 302. The switch may comprise a plurality of switches. The switch may comprise a switch network. The switch may comprise a multiplexer (mux). The switch may comprise a demultiplexer (demux). The switch may comprise a plurality of muxes. The switch may comprise a plurality of demuxes.

When transducer array 301 receives ultrasonic waves reflected by objects in the region of interest), transducer array 301 generates RF signals based on the reflected ultrasonic waves. The reflected ultrasonic waves may also be referred to as ultrasonic echoes, or ultrasound echoes, or echoes. The RF signals may also be referred to as raw RF data.

Reception of the ultrasound signals is controlled by a receive (Rx) beamformer 310. The Rx beamformer can comprise a table 312. The table can comprise a flag table or a compressed flag table, as discussed herein. The Rx beamformer can comprise a table decoder 316, as described herein. The table decoder can comprise a flag table decoder, as described herein. The Rx beamformer 310 can be communicatively coupled to an Rx front-end unit 314. In some implementations, Rx front-end unit 314 amplifies and digitizes the RF signals from transducer array 301 (after the signal is selected in the direction from the transducer 301 to the Rx front-end unit 314 by the switch 302) to provide RF samples, and sends the RF samples to table decoder 316 of Rx beamformer 310. The RF samples may also be referred to as digitized RF signals. The Rx front-end unit 314 may comprise an analog-to-digital (A/D) converter (ADC). The A/D converter may comprise a resolution of at least 2 bits, at least 4 bits, at least 8 bits, at least 16 bits, at least 32 bits, at least 64 bits, or at least 128 bits. The A/D converter may comprise at least 1 channel, at least 2 channels, at least 4 channels, at least 8 channels, at least 16 channels, at least 32 channels, at least 64 channels, or at least 128 channels. In some implementations, Rx front-end unit 314 amplifies and/or filters the RF signals before digitizing them. In some implementations, the amplifier gain of Rx front-end unit 314 may vary over time, in order to compensate for ultrasound attenuation.

In various implementations, Rx beamformer 310 can generate raw image data based on the RF samples, where the Rx beamformer 310 performs beamforming functions in order to generate the raw image data. The Rx beamformer 310 can create an intensity map of the reflected ultrasonic waves corresponding to every point in the field of view. Rx beamformer 310 can map the received signal to a location in an image and coherently sum the signals from all transducer elements for every point in the field of view. Various implementations of Rx beamformer 310 generating raw image data are described in more detail herein.

Given a high enough sampling rate, one or more of the transducers may receive a plurality of RF samples corresponding to an ultrasound signal emanating from a particular location in a region of interest. In the far field, this may occur when the sampling rate is greater than twice the spacing between pixels in an image line divided by the speed of sound. Each of the plurality of RF samples corresponding to the ultrasound signal from the location may be regarded as conveying information about the location that is at least partially redundant. Thus, any one of the plurality of RF samples corresponding to the ultrasound signal from the location may be sufficient to reconstruct image information for that location. The Rx beamformer may therefore select to utilize only a fraction of the RF samples corresponding to the ultrasound signal from the location. The Rx beamformer may select to utilize one or more of the RF samples in order to reconstruct image information for the location. For instance, the Rx beamformer may select to utilize the RF sample that is closest to the center of a given pixel. Utilizing only a fraction of the RF samples may allow for a reduction in the memory requirements for the handheld ultrasound device.

The Rx beamformer 310 can determine which of the RF samples are to be used to generate raw image data based on table 312. As described in more detail herein, table 312 can indicate which RF samples are to be used to generate raw image data and which RF samples are not to be used to generate raw image data. The table can be predetermined in that information in the table is generated prior to an imaging session. During runtime, the Rx beamformer can check the table during an imaging session in order to determine which RF samples to use to generate raw image data. Implementations of the table are described in more detail herein.

The table 312 may be predetermined in that information in table 312 is generated prior to an imaging session, and table 312 may be pre-loaded in Rx beamformer 310 or in any other suitable storage location. Table 312 may also be referred to as predetermined table 312. During runtime, Rx beamformer 310 can check table 312 during an imaging session in order to determine which RF samples to use to generate raw image data. In various implementations, Rx beamformer 310 generates raw image data based on the RF samples that are to be used to generate raw image data, and then sends the raw image data to image processor 318.

As indicated herein, image processor 318 processes the raw image data to provide the processed image data. The processed image data may be referred to as post-processed image data. The processed image data may in turn be used to provide ultrasound images.

As described more detail herein, in various implementations, image processor 318 determines input values based on the raw image data from Rx beamformer 310. Image processor 318 may determine output values based on the input values and a table 320 (e.g., by using a compression circuitry). In various implementations, image processor 318 compresses the raw image data such that the dynamic range of the processed image data is smaller than the dynamic range of the raw image data.

In various implementations, table 320 is predetermined in that information in table 320 is generated prior to an imaging session, and table 320 is pre-loaded in image processor 318 or in any other suitable storage location. Table 320 may also be referred to as predetermined table 320. During runtime, image processor 318 checks table 320 during an imaging session in order to determine the output values used to generate processed image data. Various implementations of table 320 are described in more detail herein.

In various implementations, sensors 322 may include position sensors, rotational sensors, tilt sensors, gyroscopes, accelerometers, etc., for positioning ultrasound device 200. In some implementations, the position sensors and rotational sensors may be integrated.

In various implementations, peripherals 326 may include one or more display devices and/or may send processed image data to remote display devices (e.g., a 2D display, a 3D display, a printer, a wearable device, an augmented-reality glass, a virtual-reality glass, etc.). Remote display devices may include stand-alone computers, tablet computers, smartphones, dedicated monitors, etc. In some implementations, peripherals 326 may also include an electrocardiograph (ECG or EKG device), pulse oximeter, position tracker, needle guide, etc. Peripherals 326 may include wireless communication circuitry, as described elsewhere herein.

Wireless communication circuitry may comprise a Wi-Fi chip with a buffer. The wireless communication may have an average maximum bandwidth of no more than about 60 megabits per second (Mbps), about 50 Mbps, about 40 Mbps, about 30 Mbps, about 25 Mbps, about 20 Mbps, about 15 Mbps, about 10 Mbps, about 5 Mbps, about 2 Mbps, or about 1 Mbps. The wireless communication may have an average maximum bandwidth that fluctuates during the course of operation due to network congestion, distance of wireless communication transmission, electronic or other electromagnetic interference, etc. The processor may be configured to transmit compressed ultrasound images in real time (e.g., in the range of 5 Hz to 200 Hz) at a bit rate of no more than a maximum average bandwidth of a wireless communication network, (e.g., about 60 Mbps, about 50 Mbps, about 40 Mbps, about 30 Mbps, about 25 Mbps, about 20 Mbps, about 15 Mbps, about 10 Mbps, about 5 Mbps, about 2 Mbps, or about 1 Mbps), without degradation of the spatial resolution and the frame rate of the images. Such real-time compression and transmission of ultrasound images can be achieved without degradation by performing the pixel compression process at a sufficient throughput (e.g., rate).

In various implementations, the ultrasound device may include an energy storage 328. The energy storage 328 may comprise one or more batteries, capacitors, or supercapacitors. The energy storage 328 may be configured to deliver power to the handheld ultrasound probe. At a given time, the energy storage 328 may be delivering power to one or more components, including the pulse generator 304, the A/D converter, the wireless communication circuitry or other peripherals, the processor, and/or the processor. The energy storage 328 may be configured to shut off power to one or more components when not in active use to save energy. The energy storage 328 may be configured to deliver varying amounts of voltage to each of the components, including the ultrasound transducer array (e.g., through a pulse generator 304), the A/D converter, the wireless communication circuitry or other peripherals, the processor, and/or the processor. The energy storage 328 may be configured to deliver varying amounts of power to each of the components, including the ultrasound transducer array (e.g., through a pulse generator 304), the A/D converter, the wireless communication circuitry or other peripherals, the processor, and/or the processor.

The energy storage 328 may be configured to operate in one of a plurality of power modes, e.g., normal, high-performance (e.g., with higher power draw), battery-saving (e.g., with lower power draw and performance such as a decreased spatial resolution or frame rate of ultrasound images). The energy storage 328 may be configured to be recharged from an alternating current (AC) power source (e.g., household AC socket) or from a direct current (DC) power source (e.g., another energy storage unit such as a battery). The energy storage 328 may be configured to accept one or more non-rechargeable energy storage units (e.g., non-rechargeable batteries) as a power source. The energy storage 328 may be configured to deliver in a single charge cycle (e.g., a period of operation without recharging) sufficient power to operate the handheld ultrasound probe for a period of time (e.g., a range of 30 minutes to one hour) sufficient to perform a typical ultrasound scan. The energy storage 328 may be configured to deliver in a single charge cycle (e.g., a period of operation without recharging) sufficient power to operate the handheld ultrasound probe a period of time (e.g., a range of 30 minutes to one hour) sufficient to perform a plurality of typical ultrasound scans during the course of a work day or hospital shift (e.g., 4 hours, 6 hours, 8 hours, 10 hours, 12 hours, 14 hours, 16 hours, 18 hours, 20 hours, 22 hours, or 24 hours).

The handheld ultrasound probe may comprise a housing 330. The housing 330 may support one or more of: the ultrasound transducer array 301, the switch 302, the pulse generator 304, the transmit (Tx) beamformer 308, the receive (Rx) beamformer 310, the table 312, the receive (Rx) front-end unit 314, the table decoder 316, the image processor 318, the table 320, the sensors 322, the FPGA 324, the peripherals (e.g., wireless communication circuitry) 326, and the energy storage device 328, when the housing 330 is grasped by a user. The housing 330 may enclose one or more of: the ultrasound transducer array 301, the switch 302, the pulse generator 304, the transmit (Tx) beamformer 308, the receive (Rx) beamformer 310, the table 312, the receive (Rx) front-end unit 314, the table decoder 316, the image processor 318, the table 320, the sensors 322, the FPGA 324, the peripherals (e.g., wireless communication circuitry) 326, and the energy storage device 328, when the housing 330 is grasped by a user. The housing 330 may comprise a display for outputting visual information, e.g., ultrasound images or a graphical user interface.

One or more of the components 301, 302, 304, 308, 310, 312, 314, 316, 318, 320, 322, and 326 of the ultrasound device can be implemented on an FPGA 324. In some cases, all of the components 301, 302, 304, 308, 310, 312, 314, 316, 318, 320, 322, and 326 of the ultrasound device are implemented on an FPGA. In some cases, components 308, 310, 312, 316, 318, and 320 are implemented on an FPGA. One or more of the components 301, 302, 304, 308, 310, 312, 314, 316, 318, 320, 322, or 326 of the ultrasound device can be implemented on an ASIC. In some cases, all of the components 301, 302, 304, 308, 310, 312, 314, 316, 318, 320, 322, and 326 of the ultrasound device are implemented on an ASIC. In some cases, components 308, 310, 312, 316, 318, and 320 are implemented on an ASIC. To enable ease of portability for a handheld ultrasound device, the components of the ultrasound device may be configured such that the handheld probe comprises a weight of no more than about 300 grams.

Figure 4:
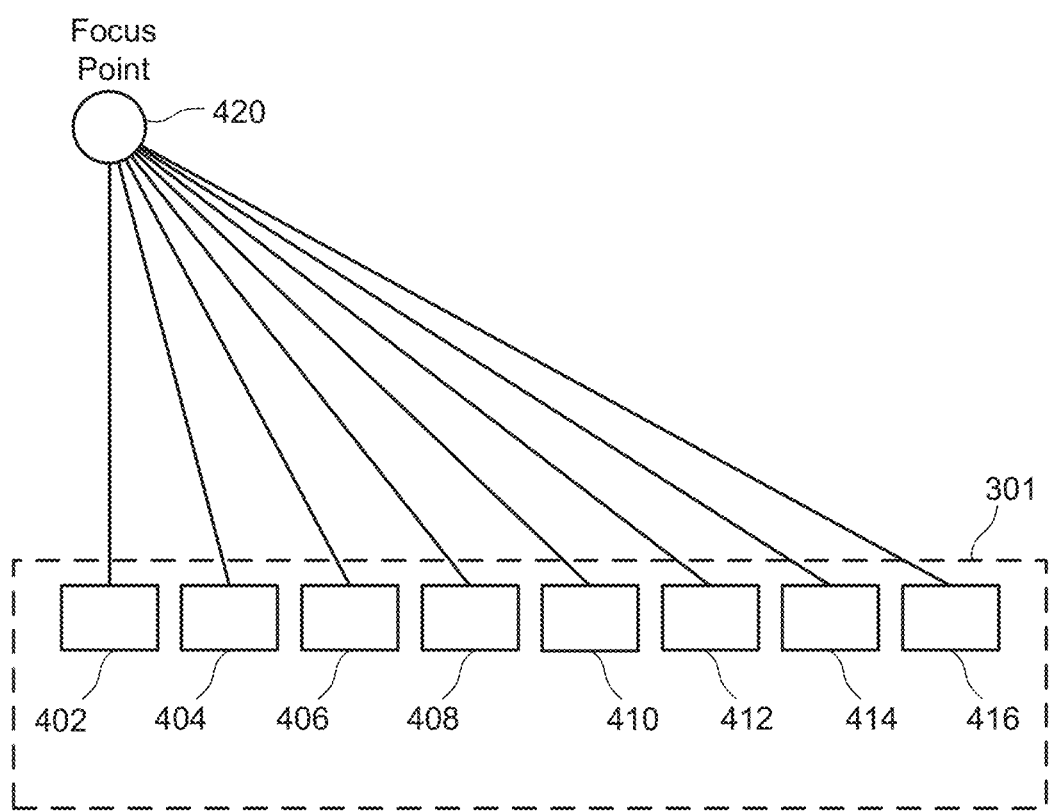
FIG. 4 shows a simplified example ultrasound transducer array.

FIG. 4 shows a simplified example ultrasound transducer array. The transducer array 301 can comprise transducer elements 402, 404, 406, 408, 410, 412, 414, and 416. The transducer elements can be piezoelectric transducer elements. The transducer elements can be capacitive transducer elements. The transducer element can be any other transducer elements as are known to one having skill in the art.

The transducer array can be any type of transducer array as is known to one having skill in the art. For example, the transducer array can be a one-dimensional array. The transducer array can be a linear sequential array. The transducer array can be a linear phased array. The transducer array can be a curved or convex sequential array. The transducer array can be an annular array. The transducer array can be a 2-dimensional array. The transducer can be a 2-dimensional rectangular array. The transducer array can include any number of transducer elements.

The transducer array shapes a beam of ultrasonic waves or pulses to give the beam a particular size and shape at various depths within a particular space beneath a surface. In some cases, the transducer array focuses ultrasonic waves to a particular location. In other cases, the transducer array produces ultrasonic waves which are not localized to a particular location. For instance, the transducer array can utilize synthetic aperture imaging. The transducer array can utilize multi-beam imaging. The transducer array can scan the ultrasound beam over the region of interest.

Regardless of the manner in which the transducer array directs ultrasonic waves at the region of interest, reflected ultrasound signals will emanate from multiple locations within the region of interest. For ease of illustration, FIG. 4 shows a single location 420 from which an ultrasound signal emanates. The ultrasound signal emanating from the location may comprise a reflected ultrasound signal.

The location can comprise a portion of a region of interest such as an organ in a person's body. Multiple locations can comprise multiple different portions of the region of interest. As such, ultrasound signals received from a set of locations allows reconstruction of an image of the region of interest.

The distance between each transducer element and each specific location, as well as the speed of ultrasound signals, can be known or predetermined. The round-trip time flight is the time it takes for an ultrasound wave to travel from one or more transmitting transducer elements to a given region of interest, to be reflected, and to be received by a transducer element. For a given signal, the transmitting transducer element can be the same as the receiving transducer element. However, transmitting transducer elements and receiving transducer elements are not necessarily the same. For example, the round-trip delay can be the one-way delay from a transmitting element to a location plus the one-way delay from the field point to a different receiving transducer element. This round-trip time of flight can be referred to as delay time. The delay time of each respective signal can be converted to a distance.

Figure 5:
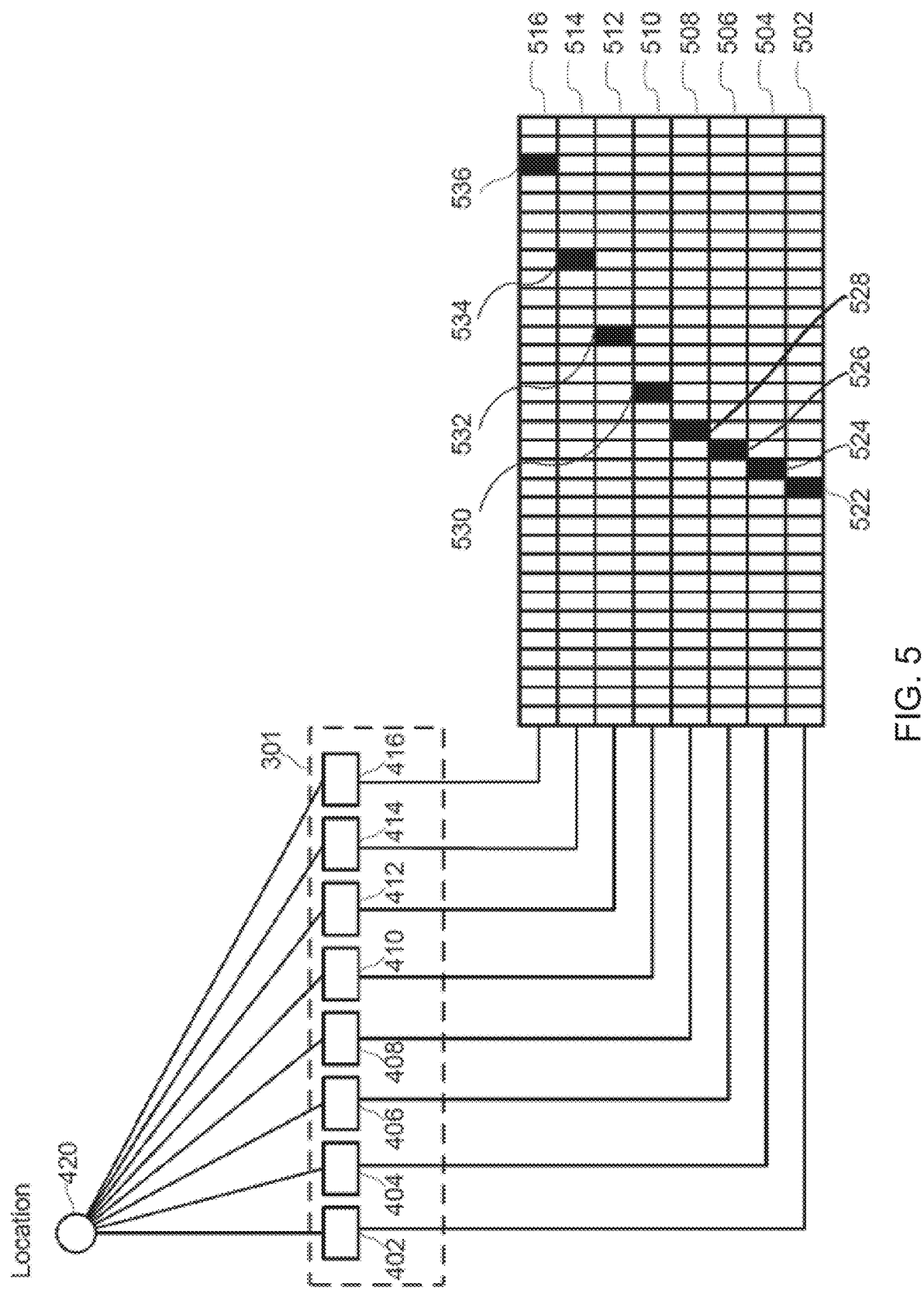
FIG. 5 shows example time delays for receipt of an ultrasound signal at each channel in an example ultrasound transducer array.

FIG. 5 shows example time delays for receipt of an ultrasound signal at each channel in an example ultrasound transducer array. Each channel in the transducer array can produce a series of RF samples over time. For instance, channel 402 can produce a series of RF samples 502. Channel 404 can produce a series of RF samples 504. Channel 406 can produce a series of RF samples 506. Channel 408 can produce a series of RF samples 508. Channel 410 can produce a series of RF samples 510. Channel 412 can produce a series of RF samples 512. Channel 414 can produce a series of RF samples 514. Channel 416 can produce a series of RF samples 516.

Due to the geometric relationships between the location and the various transducer elements, an ultrasound signal emanating from the location 420 is first received by channel 402. Prior to receipt of the ultrasound signal from the location, RF samples received at channel 402 contain no information that can be used to reconstruct one or more image pixels corresponding to that location. Such RF samples are indicated as white boxes in FIG. 5. Upon receipt of the ultrasound signal, channel 402 receives one or more RF samples 522 containing information that can be used to reconstruct one or more image pixels corresponding to the location. Such RF samples are indicated as black boxes in FIG. 5. The ultrasound signal is next received by channel 404 at a second delay time, which produces one or more RF samples 524 containing information that can be used to reconstruct one or more image pixels corresponding to the location. The ultrasound signal is received sequentially at third, fourth, fifth, sixth, seventh, and eight delay times, respectively, by channels 406, 408, 410, 412, 414, and 416. In response, channels 406, 408, 410, 412, 414, and 416 each produce one or more RF samples 526, 528, 530, 532, 534, and 536, respectively, containing information that can be used to reconstruct one or more image pixels corresponding to the location.

The schematics detailed in FIGS. 4 and 5 apply to ultrasound signals received from a single location in space. One or more of the transducers may receive ultrasound signals from a plurality of locations in space. Each such ultrasound signal may be associated with a plurality of delay times at each transducer channel.

RF samples from all receiving transducer elements can be used. That is to say, a pixel in an image can be reconstructed using multiple RF samples received by multiple transducer elements. For instance, one or more RF samples from each transducer element can be used to reconstruct a pixel in an image.

When the RF data is sampled at a high enough sampling frequency, each receiving transducer element can receive a larger number of RF samples than the number of image pixels corresponding to a line in an image for a given data acquisition. An RF sample that is used in reconstructing a line in an image can be used only once for a single pixel for each line. The Rx beamformer can determine whether each RF sample received by each channel is to be used, if at all in the reconstruction of an image or one or more pixels in an image. A used RF sample may be used for reconstruction of a fraction of the total number of image pixels. In some cases, a used RF sample may be used for reconstruction of one or more image pixels.

A trend can arise when examining the relationships between ultrasound signals obtained at a single transducer element for locations that are located near to one another. Each used RF sample received by a given transducer can be associated with a location. The locations can be indexed by image pixel index numbers. The pixel indices can be defined within each image line of an image. The pixel index can start at the location in the line that is closest to the transducer array. The pixel index can increase for locations that are further from the transducer array.

For each transducer, an RF sample received earlier in time can contribute to the reconstruction of an image pixel located closer to that transducer. For instance, the first used RF sample of a channel can be associated with the first image pixel of an image line, the second used RF sample can be associated with the second image pixel of the image line, and so on. The Rx beamformer can continuously increase the pixel index for each Rx channel.

Figure 6:
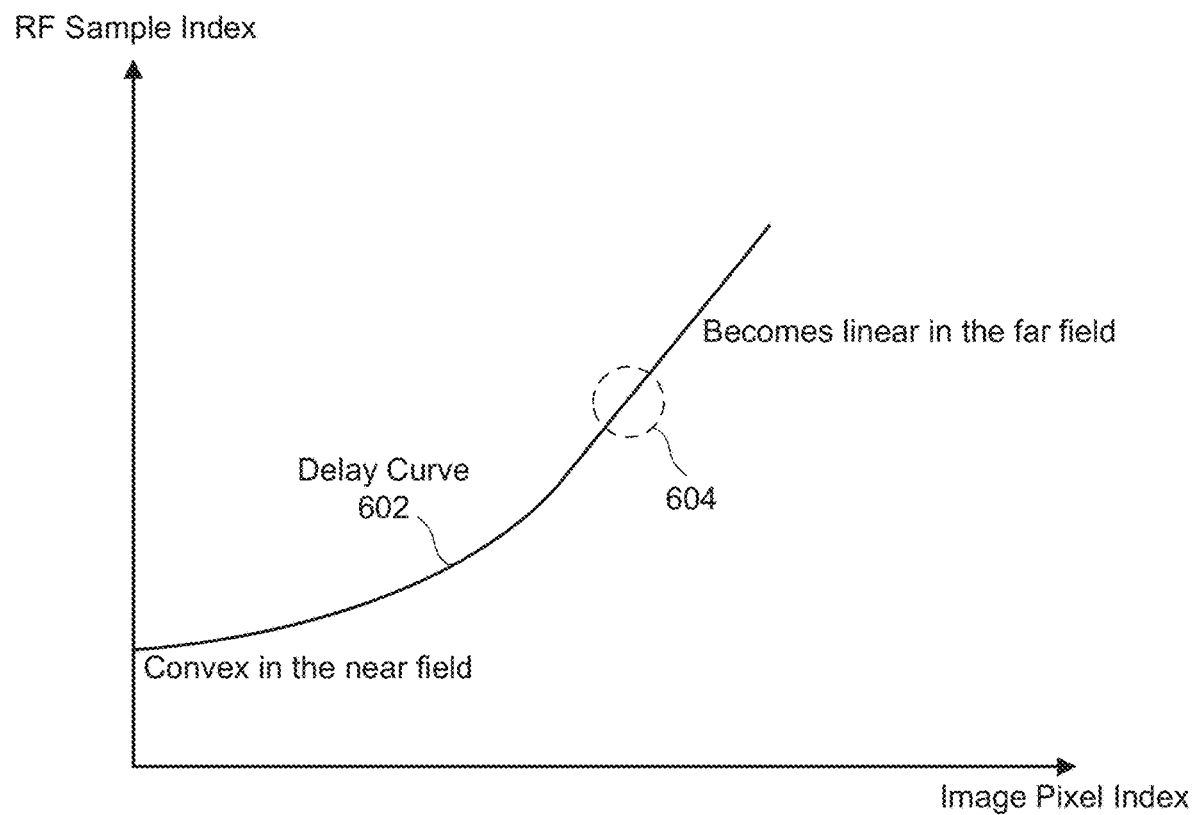
FIG. 6 shows a simplified graph of a delay curve associated with the time delays for receipt of an ultrasound signal from each location in a line, for one transducer channel.

FIG. 6 shows a simplified graph of a delay curve associated with the time delays for receipt of an ultrasound signal from each location in a line, for one transducer channel. The x-axis corresponds to the image pixel index. The y-axis corresponds to the RF sample index, or the sample number at which the ultrasound signal is received at a given transducer. The delay curve can be defined as the delay time as a function of image pixel index. The RF sample index can be approximately proportional to the delay time. In cases in which the transducer element samples at a uniform sampling rate and the image pixel spacing is uniform, the RF sample index can be proportional to the delay time. If the image pixel spacing is uniform, the delay curve 602 may be strongly non-linear in the near field for pixels characterized by small indices. If the image pixel spacing is uniform, the delay curve may become nearly linear in the far field for pixels characterized by large indices. A nearly linear portion 604 of the delay curve is described in more detail in FIG. 7.

FIG. 7 shows a simplified graph of a portion of a delay curve associated with the time delays for receipt of an ultrasound signal from each location in a line, for one transducer channel. An example of the nearly linear behavior of the delay curve in the far field is provided. In the far field, image pixels with indices 610, 611, and 612 can be associated with RF samples with indices 4700, 4708, and 4716, respectively.

In both the strongly non-linear and nearly linear portions of the delay curve, the delay time can increase monotonically with the pixel index. The combination of sparsity, periodicity, and monotonicity can allow compression of the table. This, in turn, can allow for a significant reduction in the computational resources required to carry out Rx beamforming on a handheld ultrasound device. For instance, compression of the table can allow for a significant reduction in the memory resources required to carry out Rx beamforming on a handheld ultrasound device.

The table can include positive indicators that indicate which RF samples are to be used to generate image data. The table can also include negative indicators that indicate the RF samples that are not to be used to generate image data. An indicator can associate with each RF sample received by each channel. In other words, each RF sample can be associated with either a positive indicator or a negative indicator.

The table can be referred to as a flag table. The flag table can utilize positive flags as positive indicators and negative flags negative indicators. In this manner, each RF sample can be associated with either a positive flag or a negative flag. Each indicator or flag can be a 1-bit indicator. For example, a positive indicator can be a binary "1", or a "1-flag". A negative indicator can be a binary "0", or a "0-flag". Other binary conventions can be utilized, such as assigning a 0-flag as a positive indicator and a 1-flag as a negative indicator. Alternatively, more than one bit can be used as an indicator. In such cases, any binary coding scheme can be used to assign positive and negative indicators.

For each RF sample from each channel, the RF sample can be used, or stored into a memory device, if the flag is a 1-flag. The RF sample can be discarded, or not stored into memory, if the flag is a 0-flag. An RF sample with a 1-flag and associated with an $i^{th}$ image pixel can be stored in association with the $i^{th}$ image pixel in an image line of an image buffer. In some cases, two or more RF samples (originating, for instance, from two or more channels), each with a 1-flag and associated with an $i^{th}$ image pixel, can be added together in the image buffer.

The image buffer can store image data. In some cases, the image buffer may not store an entire set of image data, but instead can store only one or more partial or complete image lines. The image buffer can store multiple lines. Once the one or more image lines have been stored within the image buffer and are ready for further processing, the image data for the one or more lines can be transferred to the image processor 318 before the beamformer starts to receive the RF samples for the next image line. Thus, it can be sufficient for the image buffer to have a memory capacity for only one image line or multiple image lines. It may not be necessary for the image buffer to have a memory capacity for the full image data.

Because all RF samples are processed immediately when they are received, there can be no need for an RF buffer. The flag table can replace a delay table which stores the delay values for all image pixels. In some cases, the flag table can require a smaller amount of memory than a delay table. Moreover, the real-time processing capability enabled by the flag table can eliminate the need for an RF buffer, further reducing the memory requirement.

FIGS. 8A and 8B show a simplified example delay table for a channel in an example ultrasound transducer array and a simplified flag table for a channel in an example ultrasound transducer array, respectively. As shown in FIG. 8A, a delay table can store a delay time for each image pixel, for each transducer element. For instance, a delay table 800 can store delay times of 4700, 4708, 4716, 4724, and 4732 for image pixels with indices of 610, 611, 612, 613, and 614, respectively. A delay table can also store delay times for image pixels with indices smaller than 610 and for image pixels with indices greater than 614. The need to store delay times can require substantial memory resources. For instance, a delay table for an ultrasound system utilizing 32 channels and 6400 RF samples per channel with an image resolution of 76×761 pixels, can require the storage of 2 bytes of data for each delay time. This can correspond to a delay table size of approximately 3.53 MB. Additionally, use of a delay table can require the use of an RF buffer. For an ultrasound system utilizing 32 channels, 6400 RF samples per channel, and 2 bytes of memory per RF sample, an RF buffer of approximately 0.4 MB can be required. Thus, the memory resources required for implementing a delay table using such an exemplary ultrasound system can total approximately 3.93 MB.

As shown in FIG. 8B, a flag table can store a 1-bit indicator for each RF sample received at each channel. For instance, a flag table 810 can store a 0-flag, 1-flag, 0-flag, 0-flag, 0-flag, 0-flag, 0-flag, 0-flag, 0-flag, 1-flag, 0-flag, 0-flag, 0-flag, 0-flag, 0-flag, 0-flag, 1-flag, and 0-flag for RF samples with indices 4699, 4700, 4701, 4702, 4703, 4704, 4705, 4706, 4707, 4708, 4709, 4710, 4711, 4712, 4713, 4714, 4715, and 4717, respectively. A flag table can also store 1-bit indicators for RF samples with indices less than 4699 or greater than 4717. A flag table can store 1-bit indicators for all RF samples received at each channel. The number of 1-bit indicators stored in a flag table can be greater than the number of delay times stored in a delay table. However, flag table can utilize fewer memory resources owing to the use of 1-bit flags in place of much larger delay times, such as 2-byte delay times. For instance, a flag table for an ultrasound system utilizing 32 channels, 6400 RF samples per channel, and 2 bytes of memory per RF sample, with an image resolution of 76×761 pixels, can require the storage of a flag table with a size of approximately 1.86 MB. The use of a flag table can obviate the need for an RF buffer. Thus, the use of a flag table can reduce the memory requirements for an ultrasound device by a factor greater than 2 compared to the use of a delay table. The exact factor may depend on the fraction of RF samples used and the amount of memory used to store each delay time in conventional beamforming. For instance, using ⅛ of the RF samples may yield a flag table with 8 times more entries than a delay table utilized in conventional beamforming. However, each entry in the flag table may occupy only 1 bit, compared to 16 bits in a delay table. Thus, the flag table may reduce the overall memory requirements by a factor greater than 2 in this example. The used RF samples can comprise no more than about 1% of the total number of RF samples, no more than about 2% of the total number of RF samples, no more than about 5% of the total number of RF samples, no more than about 10% of the total number of RF samples, no more than about 20% of the total number of RF samples, or no more than about 50% of the total number of RF samples. The used RF samples can comprise a portion of the total number of RF samples within a range defined by any two of the preceding values.

Delay times can be pre-calculated based on every distance from each transducer element to each focus point in space that is to be reconstructed. Each delay time can be saved in a look-up table. Each receiving transducer element can have a predetermined delay time associated with each location in a space being imaged. The delay times can be stored in advance of imaging. Similarly, the flag table, which is constructed from the delay times, can be stored in advance of imaging. The flag table can then be later accessed during operation. In some cases, the flag table may not change as long as the geometry of the imaging space, the transducer array, and/or the imaging scheme do not change.

To determine which of the RF samples are to be used to generate image data, the Rx beamformer can determine which of the RF samples are associated with positive indicators in the flag table. In such a determination, positive indicators can indicate the RF samples that are to be used to generate image data. For example, if a given RF sample is associated with a 1-flag in the flag table, that RF sample can be used to generate image data. Accordingly, the Rx beamformer can send incoming RF samples associated with a 1-flag to the image buffer.

To determine which of the RF samples are not to be used to generate image data, the Rx beamformer can determine which of the RF samples are associated with negative indicators in the flag table. In such a determination, negative indicators can indicate the RF samples that are not to be used to generate image data. For example, if a given RF sample is associated with a 0-flag in the flag table, that RF sample may not be used to generate raw image data. Accordingly, the Rx beamformer can ignore incoming RF samples associated with a 0-flag.

The Rx beamformer can send the RF samples that are to be used to generate image data to an image buffer, where the RF samples that are to be used to generate image data are added to the corresponding image pixel in the image buffer. The index of the corresponding image pixel can be one more than the number of RF samples in this Rx channel that have been used so far. The Rx beamformer can send each RF sample associated with a positive indicator to the image buffer immediately after acquisition of that RF sample.

An RF sample can be received by each channel at every data clock. The Rx beamformer can check the indicator or flag for the current RF sample. If the flag is a 0-flag, the Rx beamformer can discard the RF sample. If the flag is a 1-flag, the Rx beamformer can send the RF sample to an image buffer. The first used RF sample of the channel can be added to the first pixel in the image line of the image buffer, and the following used RF samples can be added to the following pixels in the image line of the image buffer, in the order of arrival.

When the slowest channel receives the RF sample for a given pixel, the RF samples from all channels for this pixel can be summed to calculate the image value of this pixel. For instance, the slowest channel can be one of the two edge channels, or the first or last transducer in a line of transducers. Thus, the Rx beamformer can only need to check the progress of the two edge channels. When the two edge channels receive RF samples for a given pixel, the Rx beamformer can presume that all other channels have received RF samples for the pixel.

The Rx beamformer can discard the RF samples that are not to be used to generate image data. By not storing the RF samples that are not to be used to generate image data, the memory consumption can be reduced.

The 1-flags and 0-flags in the flag table can have a characteristic pattern of bits, and this pattern can be used to compress the flag table further. The flag table can be compressed in order to further reduce memory consumption. The compression can occur when the flag table is constructed and before the Rx beamformer accesses the flag table during runtime. During runtime, the Rx beamformer can decode the compressed flag table in order to determine which of the RF samples are to be used to generate raw image data. The flag table can be decoded in real time, so as to determine which RF samples to use in real time.

The flag table can include a predetermined pattern of positive indicators and negative indicators which can be substantially periodic. The periodicity can be especially pronounced in the far field. The periodicity can arise because, in the far field, the distances from a given transducer element to each location increases almost linearly, as a result of the uniform spacing between image pixels in an image line. Also, the delay times associated with those distances can increase substantially linearly.

As shown in FIG. 6 and FIG. 7, the delay curve becomes substantially linear in the far field. This behavior is manifested in the flag table as shown in FIG. 8B, where the number of 0-flags between two consecutive 1-flags is substantially constant for RF samples obtained from locations that are relatively far from the transducer. The relatively constant number of 0-flags between two consecutive 1-flags can allow for further compression of the flag table. The number of 0-flags between two consecutive 1-flags can be referred to as NZ. There can be a predetermined number of 0-flags between two consecutive 1-flags, and this pattern can repeat. If the delay curve were perfectly linear, then the flag table would always have the same number of 0-flags between two 1-flags. However, because the delay curve is not perfectly linear, the number of 0-flags between two 1-flags will change over the field of RF samples.

The space surrounding a given transducer element can be divided into two zones or regions. The zone relatively close to the transducer element can be referred to as the near field, and the zone further from the transducer element can be referred to as the far field. The behavior of the delay curve determines how NZ changes when moving from the near field to the far field. An initial value of NZ can be determined by the starting image depth, the transducer element location, and the angle of the image line. For instance, a shallow imaging depth will produce a relatively small initial NZ, as the difference in the distance from the region of interest to a first transducer and the distance from the region of interest to a second transducer located adjacent to the first transducer is relatively small for a shallow imaging depth. A deeper imaging depth will produce a relatively large initial NZ, as the difference in the distance from the region of interest to a first transducer and the distance from the region of interest to a second transducer located adjacent to the first transducer is relatively small for a shallow imaging depth. At near field, NZ can be relatively small. NZ can monotonically increase with distance from the transducer to a location. At far field, NZ can converge to a nearly constant number which is determined by the RF sampling rate and the image pixel spacing. Thus, for instance, NZ can converge to a value of 7 in the far field, as in FIG. 8B. NZ can converge to any positive numerical value. NZ can converge to any positive integer value.

For portions of the flag table where the delay curve is approximately linear, less information can need to be saved because information specifying the slope of the delay curve, which does not change much, can be saved instead. The value of NZ can be correlated to the slope of the delay curve. Because the delay curve is mostly linear, but not perfectly linear, the slope of delay curve can change over the region being imaged. Thus, the compressed flag table can store a representation of only the initial slope of the delay curve and the locations where the slope of the delay curve changes. As such, the compressed flag table may not need to save all 1-flags and 0-flags. This can all reduce the size of the compressed flag table.

The table decoder 316 can store the RF sample index of the first positive indicator. The table decoder 316 can assign an initial NZ based on the number of negative indicators between the two first positive indicators. The table decoder 316 can assume that the next positive indicator will be attained after NZ negative indicators. The table decoder 316 can examine the flag table to determine whether this behavior is observed. If the flag table fails to conform to this behavior, the table decoder 316 can alter the value of NZ in order to account for the non-linear behavior of the delay curve. If a negative indicator is observed when a positive indicator is expected, the table decoder 316 can alter the value of NZ by increasing this value. If a positive indicator is observed when a negative indicator is expected, the table decoder 316 can regard this behavior as an exception and leave NZ at its present value.

The predetermined pattern can be related to the slope of the delay curve. Information about the slope can be stored in the compressed flag table. The delay curve can be defined as the delay time as a function of image pixel index. The slope information can be predetermined and already stored in the compressed flag table before imaging. The slope can be equivalent to NZ, as NZ=round(slope−1).

The table decoder 316 can start with the index of the first 1-flag and an initial NZ for the first two 1-flags. The table decoder 316 can then scan the flag table, expecting a 1-flag after every NZ 0-flags based on the predetermined pattern. In some cases, a flag may not match this expectation. Such a disagreement between the position of the 1-flag predicted by NZ and the actual position of the 1-flag can indicate that the slope of the delay curve has changed or there has been a quantization error. The beamformer can only need to store the index of each flag at which this disagreement occurs. This can compress the data in the flag table.

Owing to the nature of the delay curve, the number of 0-flags between two 1-flags can only increase with larger and large pixel index. As such, when there is an unexpected 0-flag, it can be assumed that the slope has increased. Thus, when there is an unexpected 0-flag, the table decoder 316 can monotonically increase NZ by 1, as more 0-flags between two 1-flags can be expected from the functional form of the delay curve. The next flag can be expected to be a 1-flag.

In some cases, an unexpected 1-flag can occur such that there are fewer 0-flags between two 1-flags than expected from NZ. The functional form of the delay curve can lead to a belief that this should not happen. Thus, in such a case, a quantization error can be presumed. An unexpectedly early 1-flag can be considered an exception. In the case of an unexpectedly early 1-flag, the flag table encoder can keep the current NZ. The table decoder 316 can store the exception. The next flag can be expected to be a 0-flag. The table decoder 316 can continue scanning until the last flag has been checked.

The aforementioned activities can produce a compressed flag table. The compressed flag table can comprise an index of the RF sample at which the first 1-flag occurs, an initial NZ, and a list of the indices of RF samples that do not match the expected pattern. The list of RF sample indices that do not match the expected pattern can comprise a list of unexpected 0-flags and unexpected 1-flags. Since the compressed flag table can store only a few pieces of information that specify the full pattern of 1-flags and 0-flags in the flag table, as opposed to a full list of 1-flags and 0-flags stored in the flag table, the compressed flag table can be further substantially reduced in size. For instance, a compressed flag table for an ultrasound system utilizing 32 channels and 6400 RF samples per channel, with an image resolution of 76×761 pixels, can require only approximately 68 kB of storage space. This can be compared to storage space of approximately 1.86 MB for the full flag table and 3.93 MB for a delay table for an ultrasound system operating with the same parameters. Thus, the compressed flag table can reduce the storage requirements by a factor of greater than 25 compared to the full flag table and by a factor of greater than 50 compared to the delay table. The compressed flag table can reduce the storage requirements by a factor of greater than 5, greater than 10, greater than 50, greater than 100, greater than 250, greater than 500, or greater than 1000 compared to the full flag table. The compressed flag table can reduce the storage requirements by a factor of greater than 5, greater than 10, greater than 25, greater than 100, greater than 250, greater than 500, or greater than 1000 compared to the delay table.

The Rx beamformer can decode the compressed flag table at runtime. The first data entries in the compressed flag table can comprise the index of the first used RF sample and an initial NZ. The beamformer can utilize a counter to track the number of 0-flags that have occurred since the last 1-flag. In some cases, no RF sample is stored until the current RF sample index reaches the index of the first used RF sample. When the current RF sample index reaches the value of the first index, the RF sample can be stored to the first image pixel location in the image buffer. The Rx beamformer can then skip the next NZ samples before storing an RF sample to the next location in the image buffer, which can occur when the counter reaches the value of the next index stored in the compressed flag table. The Rx beamformer can account for indices that do not match the expected flag pattern based on the value of NZ. For instance, if the beamformer notes an unexpected 1-flag before the counter reaches a count of NZ, this can indicate a quantization error. In such case, the sample can be stored to the image buffer and the Rx beamformer can start counting the number of 0-flags until the counter again reaches NZ. If the beamformer notes an unexpected 0-flag when the counter reaches NZ, this can indicate a change in the slope of the delay curve. In such case, the sample can be discarded and the beamformer can increase the value of NZ by one. This process can be repeated until the last pixel in the image line is reconstructed.

Figure 9:
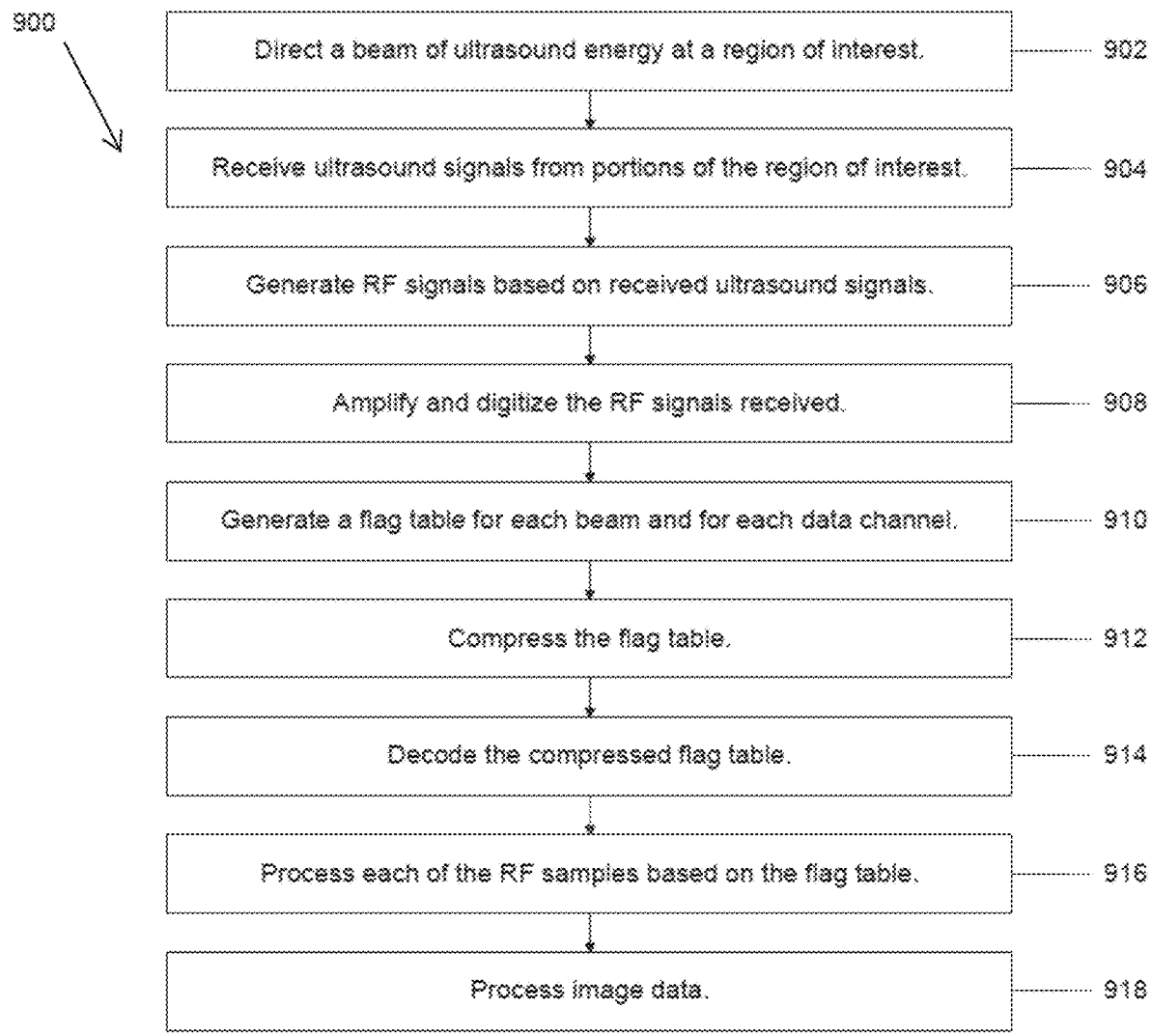
FIG. 9 shows a flowchart of a method for ultrasound beamforming using a flag table or compressed flag table.

FIG. 9 is a flowchart of a method for ultrasound beamforming using a flag table or compressed flag table. The method 900 consists of the steps of directing a beam of ultrasound energy at a region of interest, receiving ultrasound signals from portions of the region of interest, generating RF signals based on received ultrasound signals, amplifying and digitizing the RF signals received, generating a flag table for each beam and for each data channel, optionally compressing the flag table, optionally decoding the compressed flag table, processing each of the RF samples based on the flag table, and processing image data to provide processed image data.

In step 902, one or more beams of ultrasound energy are directed at a region of interest. The one or more beams can generate ultrasound signals along a scanline corresponding to a line in an image. The scanline can be defined by a trajectory of the one or more beams through the region of interest.

In step 904, ultrasound signals are received from portions of the region of interest. The ultrasound signals can arise from reflections of the ultrasound energy from portions of the region of interest that lie along a scanline of the one or more beams. The ultrasound signals can be received by one or more ultrasound transducers in one or more ultrasound transducer arrays. Each of the one or more ultrasound transducers can be referred to as a data channel.

In step 906, RF signals are generated based on the received ultrasound signals. The received signals can arise from reflections of the ultrasound energy from portions of the region of the interest that lie along a scanline of the one or more beams. The RF signals can be generated by causing each of the one or more transducers to vibrate.

In step 908, the RF signals received from the plurality of channels are amplified and digitized. The RF signals can be sampled to provide RF samples at an RF sampling rate that is associated with a data clock. The data clock can have a clock cycle. At each clock cycle, an RF sample can be received by each of the one or more data channels. Each RF sample can be associated with an ultrasound signal emanating from a location along a scanline of the one or more beams.

In step 910, a flag table is generated for each beam and for each data channel. The flag table can comprise an RF index and a flag associated with each of the RF samples. The flag table may comprise an ordered list of flags. The ordering may correspond to the RF sample index. For instance, the first flag may correspond to the first RF sample index, the second flag may correspond to the second RF sample index, etc. The RF sample index can correspond to a delay time associated with receiving an RF sample. The delay time can be based on the data clock. Each flag can be a single-bit binary flag indicator. Each binary flag indicator can have a positive or a negative value. The positive value can comprise a 1-flag. The negative value can comprise a 0-flag.

In step 912, the flag table is compressed. The compression of the flag table can comprise the step of assigning an initial NZ based on the number of negative binary flag indicators occurring between the first and second positive binary flag indicators in the flag table. The compression can further comprise assuming that the next positive indicator will be attained after NZ negative indicators and examining the flag table to determine whether this behavior is observed. The compression can further comprise storing the index of the flag at which an expected value failed to occur if the flag table fails to conform to this behavior. If an unexpected 1-flag occurs, the compression can comprise storing the index of the unexpected 1-flag. If an unexpected 0-flag occurs, the compression can comprise storing the index of the unexpected 0-flag and incrementing the value of NZ. The compression can comprise continuing to scan the flag table until the last flag has been checked.

In step 914, the compressed flag table is decoded. The decoding of the compressed flag table can comprise noting the index of the first used RF sample and an initial NZ. The decoding of the compressed flag table can further comprise utilizing a counter to track the number of 0-flags that have occurred since the last 1-flag. The decoding of the compressed flag table can further comprise storing a first used RF sample to a first image pixel location in an image buffer when the current RF sample index reaches the value of the first used RF sample index. The decoding of the compressed flag table can further comprise skipping the next NZ samples before storing an RF sample to the next location in the image buffer when the counter reaches NZ. The decoding of the compressed flag table can further comprise accounting for indices that do not match the flag pattern expected from the value of NZ. The decoding of the compressed flag table can further comprise storing a sample to the image buffer when an unexpected 1-flag is encountered before the counter reaches a count of NZ. The decoding of the compressed flag table can further comprise discarding a sample when an unexpected 0-flag is encountered when the counter reaches a value of NZ and incrementing the value of NZ. The decoding of the compressed flag table can further comprise repeating this process until the last pixel in the image line is reconstructed.

In step 916, each of the RF sample is processed based on the flag table. The processing can occur for each data channel and for each ultrasound beam directed to the region of interest. The data channels can comprise one or more edge channels characterized by being located at a farthest point from the center of the transducer array. The data channels can comprise two edge channels. For instance, a linear transducer array may comprise two edge channels corresponding to the ends of the linear array. The data channels can comprise more than two edge channels. For instance, a square transducer array may comprise four edge channels corresponding to the corners of the square array. In another example, a circular transducer array may compromise a plurality of channels located on an outermost radius of the circular array. The data channels can comprise zero edge channels. For instance, an annular array may have all channels located at the same distance from a center of the array and therefore may have no edge channels.

The processing can comprise receiving an RF sample at a first clock cycle of the data clock. The RF sample can be associated with a location along a scanline defined by a trajectory of one or more ultrasound beams through a region of interest. The processing can further comprise sending the RF sample to a first pixel in a per-channel image buffer if the flag associated with the received RF sample has a positive indicator value. The processing can comprise sending the RF sample to a first pixel in a per-channel image buffer only if the flag associated with the received RF sample is the first positive flag. The processing can further comprise discarding the received RF sample if the flag associated with the received RF sample has a negative indicator value. The processing can further comprise receiving a subsequent RF sample corresponding to a next clock cycle of the data clock. The processing can further comprise sending the subsequent RF sample to a first pixel in a per-channel image buffer if the flag associated with the subsequent RF sample has a positive indicator value. The processing can comprise sending the subsequent RF sample to a first pixel in a per-channel image buffer only if the flag associated with the received RF sample is the first positive flag. The processing can further comprise discarding the subsequent RF sample if the flag associated with the subsequent RF sample has a negative indicator value. The processing can further comprise repeating receiving and either retaining or discarding each subsequent RF sample until one of the edge channels receives the RF samples corresponding to the last image pixel in an image pixel line. The processing can further comprise adding the RF samples corresponding to a pixel from all data channels to generate an image value for the pixel.

In step 918, the image data is processed to provide processed image data. The processing can comprise any processing as is known to one having skill in the art.

The method 900 can produce a maximum delay error that is no more than half of an RF sampling period The method 900 can allow a decision about whether an RF sample is to be used for a certain pixel or not in less than one RF sampling clock cycle after the data sample is captured.

A person of ordinary skill in the art will recognize many variations, alterations and adaptations based on the disclosure provided herein. For example, the order of the steps of the method 900 can be changed, some of the steps removed, some of the steps duplicated, and additional steps added as appropriate. Some of the steps can be performed in succession. Some of the steps can be performed in parallel. Some of the steps can be performed once. Some of the steps can be performed more than once. Some of the steps can comprise sub-steps. Some of the steps can be automated and some of the steps can be manual. The processor as described herein can comprise one or more instructions to perform at least a portion of one or more steps of the method 900.

Figure 10:
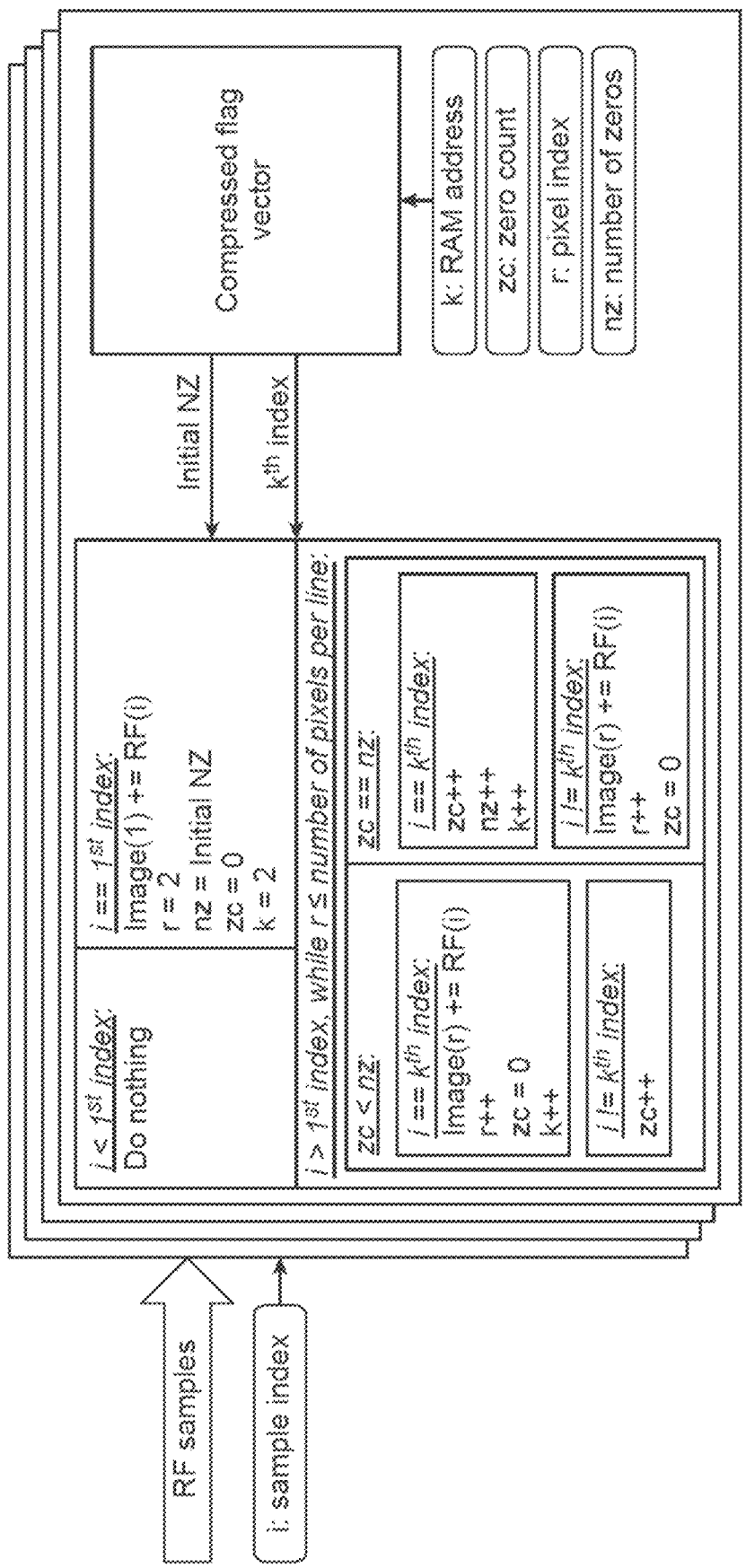
FIG. 10 shows example pseudocode for implementing flag table based ultrasound beamforming.

FIG. 10 shows example pseudocode for implementing flag based ultrasound beamforming. The pseudocode utilizes variables k (corresponding to a RAM address), zc (corresponding to a counter of the number of adjacent 0-flags counted), r (corresponding to a pixel index), and nz (corresponding to expected number of zeros to be encountered between two 1-flags). The variable nz corresponds to the value NZ described herein. The pseudocode can process RF samples and can utilize an index i corresponding to the current index of each RF sample. The pseudocode can perform real-time decompression of the compressed flag table to select which RF samples are to be used to reconstruct an image.

When the RF sample index i is smaller than the $1^{st}$ RF sample index, the pseudocode does nothing. When the RF sample index i is made equal to the $1^{st}$ RF sample index, the pseudocode adds the value of the RF sample to a first pixel in an array of image pixels. The pseudocode then increments r to move to the next pixel. The pseudocode resets the value of the counter zc to 0. The pseudocode increments the value of k to a second RAM address.

For values of i greater than the $1^{st}$ RF sample index, the pseudocode compares zc to nz. When zc is smaller than nz and i is equal to the $k^{th}$ RF sample index stored in the compressed flag table (or vector), an unexpected 1-flag has been encountered, and the pseudocode adds the value of the RF sample to the $r^{th}$ pixel in an array of image pixels. The pseudocode then increments r to move to the next pixel and resets the value of the counter zc to 0. The pseudocode increments the value of k to the next RAM address (corresponding to the next RF sample). When zc is smaller than nz and i is not equal to the $k^{th}$ RF sample index, an expected 0-flag has been encountered, and the pseudocode increments zc.

When zc is equal to nz and i is equal to the $k^{th}$ RF sample index stored in the flag table, an unexpected 0-flag has been encountered, and the pseudocode increments zc, nz, and k. When zc is equal to nz and i is not equal to the $k^{th}$ RF sample index stored in the flag table, an expected 1-flag has been encountered, and the pseudocode adds the value of the RF sample to the $r^{th}$ pixel in an array of image pixels. The pseudocode then increments r to move to the next pixel and resets the value of the counter zc to 0.

Figure 11:
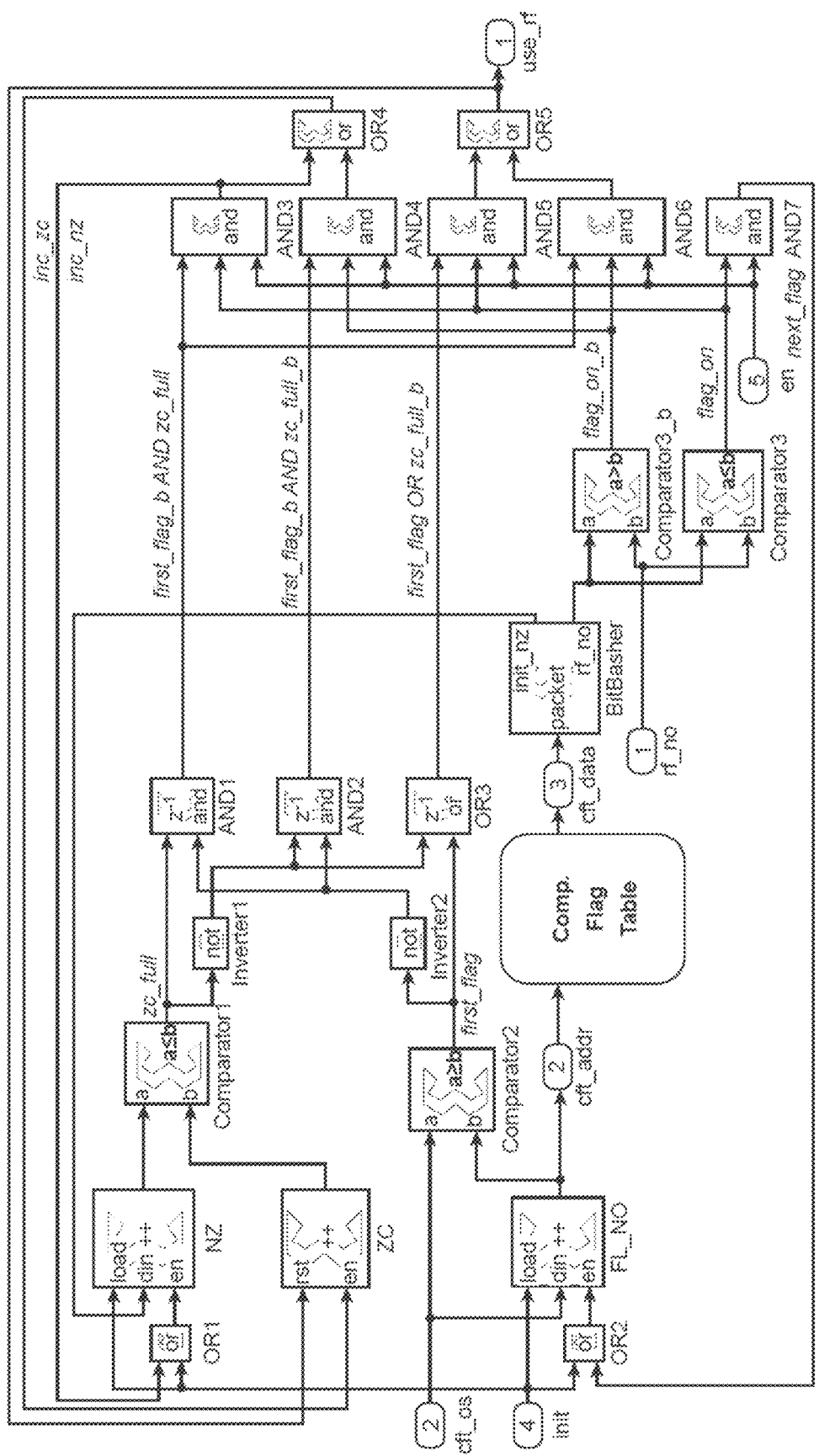
FIG. 11 shows example circuitry for implementing flag table based ultrasound beamforming.

FIG. 11 shows example circuitry for implementing flag based ultrasound beamforming with a compressed flag table. The circuitry comprises a compressed flag table (CFT), OR gates (OR1, OR2, OR3, OR4, and OR5), counters (ZC, NZ, and FL_NO), comparators (Comparator1, Comparator2, Comparator3, and Comparator 3b), NOT gates (Inverter1 and Inverter2), AND gates (AND1, AND2, AND3, AND4, AND5, AND6, AND7), and a BitBasher. The circuitry depicted in FIG. 11 is a direct implementation of the pseudocode described in FIG. 10 followed by logic reduction. Hence, the circuitry depicted in FIG. 11 may perform an identical functionality as the pseudocode described in FIG. 10, namely, implementing flag table based ultrasound beamforming with a compressed flag table.

Once the flag based ultrasound beamforming procedure is complete, the image processor 318 may perform various operations to generate processed image data, e.g., image compression. This generation may be based on raw image data received from Rx beamformer 310 in order to provide ultrasound images. In various implementations, to process the raw image data to provide processed image data, image processor 318 compresses the raw image data such that the dynamic range of the processed image data is smaller than the dynamic range of the raw image data.

An image compression method is initiated when image processor 318 determines input values based on raw image data from Rx beamformer 310, where the input values fall within a dynamic range of input values (e.g., $[0, (2^{32}-1)]$ for a 32-bit input). In some implementations, the dynamic range of input values includes dynamic subranges. In some implementations, the dynamic range of input values may have a predetermined number of dynamic subranges (e.g., 2, 4, 8, 16, 32, 64, 128, 256, 512, etc.). The dynamic subranges may be a set of intervals (e.g., unequally spaced, equally spaced, or approximately equally spaced) such that the predetermined number of dynamic subranges spans the dynamic range of input values (e.g., $[0, (2^{31}-1)]$ and $[2^{31}, (2^{32}-1)]$ for a 32-bit input and 2 dynamic subranges).

The image processor 318 may determine output values based on the dynamic subranges in which the input values fall. As described in more detail herein, in some implementations, there may be 256 dynamic subranges into which one or more input values may fall. Depending on the selection of compression function, a given dynamic subrange may contain no input values. Each output value is one of 256 output values (e.g., integers from 0 to 255), where each output value corresponds to one of the 256 dynamic subranges.

For example, if there are 32 input bits and 8 output bits, an example compression function may be $f(x)=8 \log_2(x+1)-1$. This will map an input value of $2^{32}-1$ ($FFFFFFFF_{16}$) to an output value of 255. Setting the output value to 1 and solving for x, we observe that the first threshold value for such a compression function may be 1 (e.g., 0.19 rounded up to the nearest integer value). The second threshold value may be calculated by setting the output value to 2 and solving for x, and so on to generate the entire set of threshold values. Each dynamic subrange may be defined by a range of integers between two successive threshold values. Examples of dynamic subranges and output values are listed in Table 1 below.

image processor 318 determining output values are described in more detail herein.

As described in more detail herein, image processor 318 provides the processed image data, which is high-quality image data, yet with a small dynamic range. Image processor 318 may then send the processed image data to a display device to display an ultrasound image to a user.

The image processor 318 may generate the processed image data based on the output values. The processed image data may be the output values (e.g., pixel data). The processed image data may be generated based on the output values (e.g., by contrast enhancement or other image processing techniques prior to displaying the image data). Various implementations directed to image processor 318 generating the processed image data based on the output values are described in more detail herein.

Figure 12:
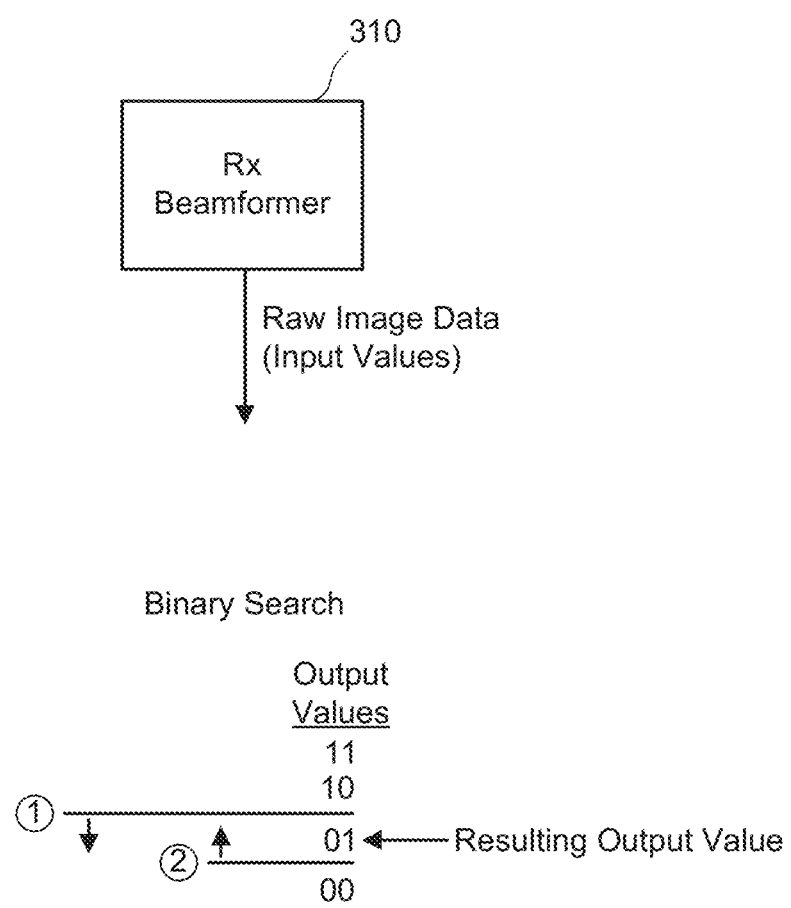
FIG. 12 illustrates an example block diagram for performing a binary search, according to some embodiments.

FIG. 12 illustrates an example block diagram for performing a binary search, according to some implementations. As shown, Rx beamformer 310 provides raw image data, which includes input values, to image processor 318.

In various implementations, to generate processed image data, image processor 318 performs a binary search, where the binary search identifies a dynamic subrange for each input value, and maps the input values to the output values based on the dynamic subranges. In other words, in various implementations, multiple input values map to a single dynamic subrange, and each dynamic subrange maps to a single output value. As such, one or more of the input values are associated with a single output value. Stated differently, each output value is associated with one or more input values (or in some cases, possibly no input values).

In some implementations, image processor 318 takes each input number and compares each to different subdynamic range thresholds in order to determine in which subdynamic range each input number falls, where each dynamic subrange maps to a particular output value.

Referring still to FIG. 12, for each input value, image processor 318 compares the input value to a first threshold value at a first stage (indicated with a circled 1 in FIG. 12). In this particular simplified example, the possible output values are 00, 01, 10, and 11. In this example, the input value is less than the first threshold value, which narrows the possible output values to 00 and 01. Image processor 318 then compares the input value to a second threshold value at a second stage. In this example, the input value is greater than the second threshold value, which narrows the possible output values to 01. As such, the resulting output value is 01. The threshold values may be calculated as described elsewhere herein.

TABLE 1

| Dynamic Subrange (Lower Bound) | 0 ($00000000_{16}$) | 14 | 234 | 60,096 | 3,938,502,375 |
|---|---|---|---|---|---|
| Dynamic Subrange (Upper Bound) | 1 ($00000001_{16}$) | $2^4 - 1$ (15) ($0000000F_{16}$) | $2^8 - 1$ (255) ($000000FF_{16}$) | $2^{16} - 1$ (65,535) ($0000FFFF_{16}$) | $2^{32} - 1$ (4,294,967,295) ($FFFFFFFF_{16}$) |
| Output Value | 1 | 31 | 63 | 127 | 255 |

As such, the overall dynamic range of input values is compressed or reduced to a smaller dynamic range of output values. One benefit of a smaller dynamic range of output values is that displays may have a smaller dynamic range. Also, the number of input values is reduced to a smaller number of output values, thereby compressing the data and memory requirements. Various implementations directed to In this simplified example, the output values are 2-bit values. As such, there are 2 stages where each input value is compared against 2 threshold values. The particular number of bits may vary, depending on the particular implementations. For example, there may be 8-bit output values, in which case there could be 8 stages where each input value is compared against 8 threshold values. In some implementations, the number of output values is limited to 256 output values (e.g., 0 to 255).

In various implementations, the function being implemented is such that the output values monotonically increase relative to the input values. In other words, a range of smaller input values correspond to a smaller output value, and a range of larger input values correspond to a bigger output value. In some implementations, the output values may monotonically decrease relative to the input values. The monotonicity of the compression function may enable a recursive binary search method to be performed with a lookup table.

Figure 13:
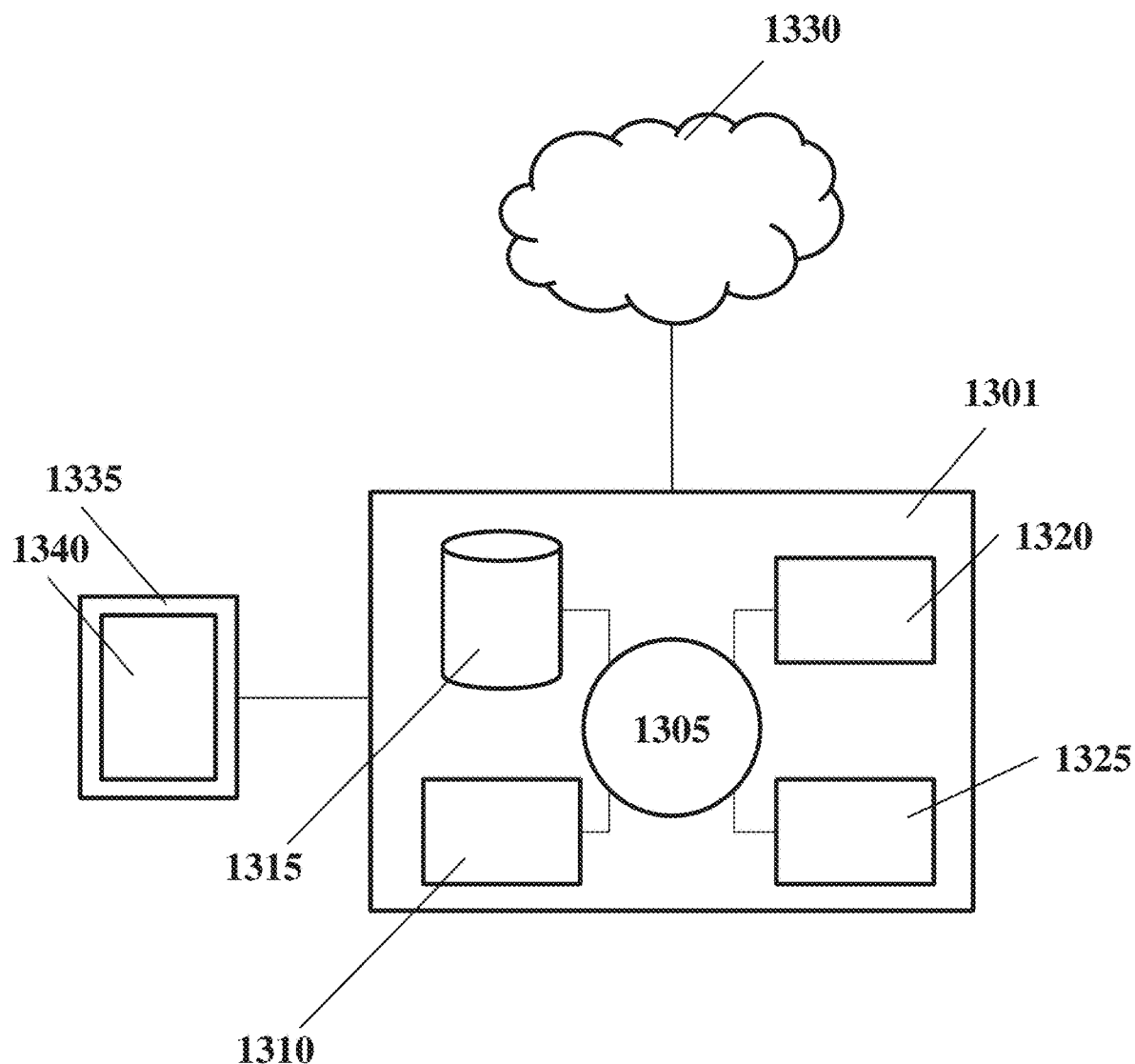
FIG. 13 shows a computer control system that is programmed or otherwise configured to implement methods provided herein.

The present disclosure provides computer control systems that are programmed to implement methods of the disclosure. FIG. 13 shows a computer system 1301 that is programmed or otherwise configured to compress ultrasound images. The computer system 1301 can regulate various aspects of ultrasound image compression of the present disclosure, such as, for example, configuring a lookup table and performing a recursive binary search method. The computer system 1301 can be an electronic device of a user or a computer system that is remotely located with respect to the electronic device. The electronic device can be a mobile electronic device.

The computer system 1301 includes a central processing unit (CPU, also "processor" and "computer processor" herein) 1305, which can be a single core or multi core processor, or a plurality of processors for parallel processing. The computer system 1301 also includes memory or memory location 1310 (e.g., random-access memory (RAM), read-only memory (ROM), flash memory), electronic storage unit 1315 (e.g., hard disk), communication interface 1320 (e.g., network adapter) for communicating with one or more other systems, and peripheral devices 1325, such as cache, other memory, data storage and/or electronic display adapters. The memory 1310, storage unit 1315, interface 1320 and peripheral devices 1325 are in communication with the CPU 1305 through a communication bus (solid lines), such as a motherboard. The storage unit 1315 can be a data storage unit (or data repository) for storing data. The computer system 1301 can be operatively coupled to a computer network ("network") 1330 with the aid of the communication interface 1320. The network 1330 can be the Internet, an internet and/or extranet, or an intranet and/or extranet that is in communication with the Internet. The network 1330 in some cases is a telecommunication and/or data network. The network 1330 can include one or more computer servers, which can enable distributed computing, such as cloud computing. The network 1330, in some cases with the aid of the computer system 1301, can implement a peer-to-peer network, which may enable devices coupled to the computer system 1301 to behave as a client or a server.

The CPU 1305 can execute a sequence of machine-readable instructions, which can be embodied in a program or software. The instructions may be stored in a memory location, such as the memory 1310. The instructions can be directed to the CPU 1305, which can subsequently program or otherwise configure the CPU 1305 to implement methods of the present disclosure. Examples of operations performed by the CPU 1305 can include fetch, decode, execute, and writeback.

The CPU 1305 can be part of a circuit, such as an integrated circuit. One or more other components of the system 1301 can be included in the circuit. In some cases, the circuit is an application specific integrated circuit (ASIC).

The storage unit 1315 can store files, such as drivers, libraries and saved programs. The storage unit 1315 can store user data, e.g., user preferences and user programs. The computer system 1301 in some cases can include one or more additional data storage units that are external to the computer system 1301, such as located on a remote server that is in communication with the computer system 1301 through an intranet or the Internet.

The computer system 1301 can communicate with one or more remote computer systems through the network 1330. For instance, the computer system 1301 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1301 via the network 1330.

Methods as described herein can be implemented by way of machine (e.g., computer processor) executable code stored on an electronic storage location of the computer system 1301, such as, for example, on the memory 1310 or electronic storage unit 1315. The machine executable or machine readable code can be provided in the form of software. During use, the code can be executed by the processor 1305. In some cases, the code can be retrieved from the storage unit 1315 and stored on the memory 1310 for ready access by the processor 1305. In some situations, the electronic storage unit 1315 can be precluded, and machine-executable instructions are stored on memory 1310.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1301 can include or be in communication with an electronic display 1335 that comprises a user interface (UI) 1340 for providing, for example, a means for user selection of a monotonic function and/or a number of output bits n. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 1305. The algorithm can, for example, perform a recursive binary search method.

Figure 14A:
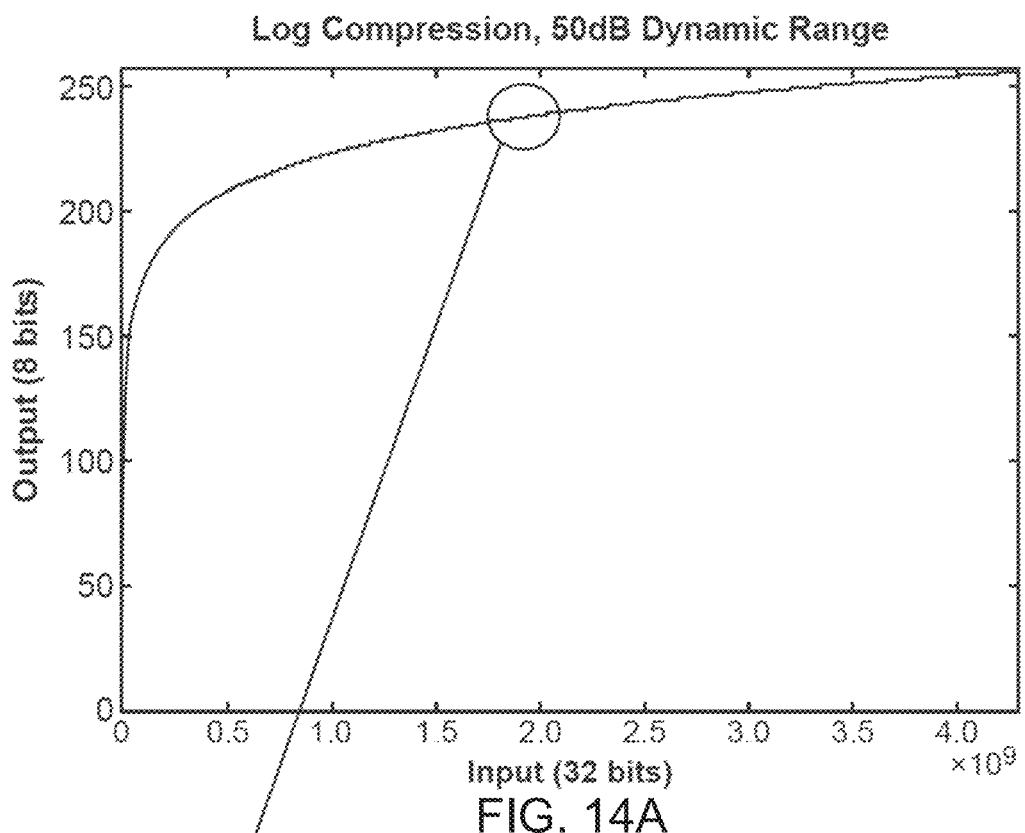
FIG. 14A shows an example of a log compression curve, which may be used for some embodiments described herein, applied on input words of 32-bit length to obtain output words of 8-bit length.
Figure 14B:
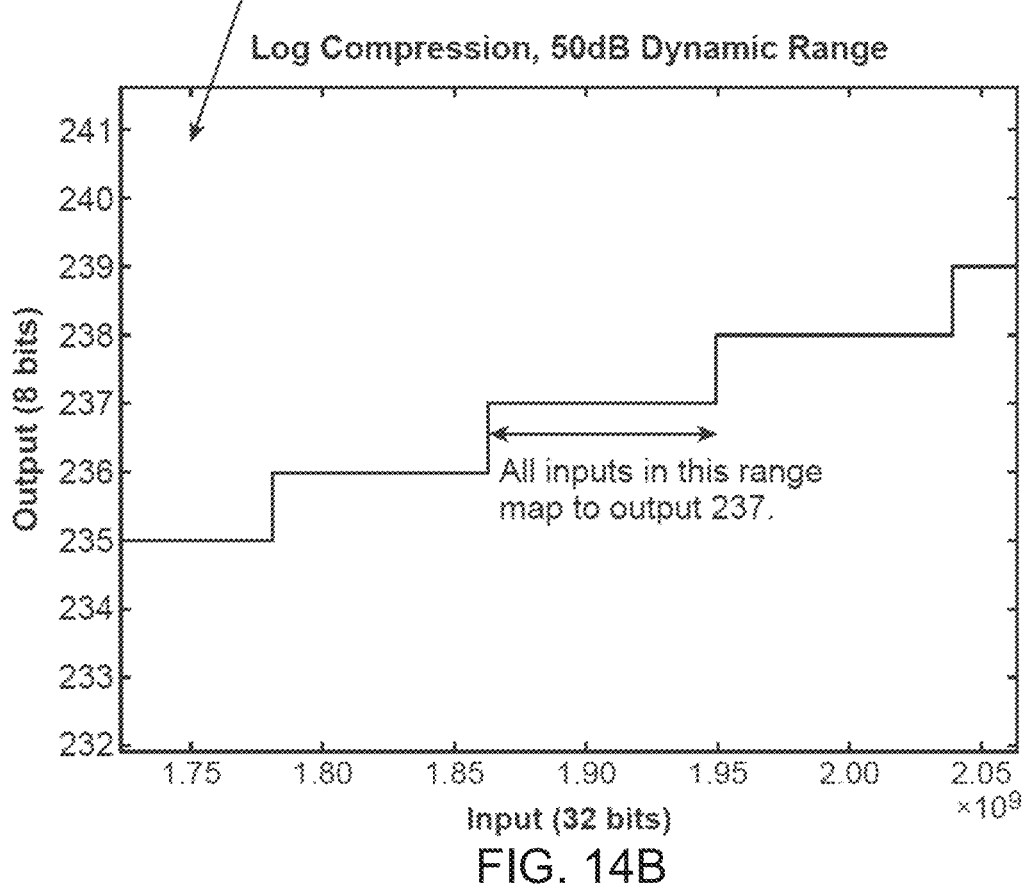
FIG. 14B shows an example of a zoomed-in portion of the log compression curve showing discrete output values corresponding to ranges of input values.

FIGS. 14A and 14B illustrate an example of a log compression curve, which may be used for some embodiments described herein. A log compression curve is used to illustrate an example of a compression curve that may be used for data compression. In general, compression curves may be monotonically increasing or decreasing over a given range of input values. The number of output bits may be less than the number of input bits.

FIG. 14A shows an example of a log compression curve applied on input words of 32-bit length to obtain output words of 8-bit length. In this example, the input words may be 32-bit length unsigned integers, and may range in value from $00000000_{16}$ (where the 16 subscript indicates values in hexadecimal or base 16) to $FFFFFFFF_{16}$ (or $2^{32}-1=4.29\times 10^9$). The output values may be 8-bit length unsigned integers, and may range in value from $00_{16}$ to $FF_{16}$ (or $2^8-1=255$). For example, for this log compression function, a 32-bit input value of $00000000_{16}$ would map to an 8-bit output value of $00_{16}=00000000_2$ (where the 2 subscript indicates values in binary or base 2), and a 32-bit input value of $FFFFFFFF_{16}$ would map to an 8-bit output value of $FF_{16}=11111111_2$. Since the size of the range of input values is about $2^{32-8}=1.68\times10^7$ times the size of the range of output values, there may be many input values (e.g., integers) that map to the same given output value (e.g., integers).

FIG. 14B shows an example of a zoomed-in portion of the log compression curve showing discrete output values corresponding to ranges of input values. This zoomed-in portion shows a range of input values of approximately $1.7\times10^9$ to $2.06\times10^9$ and a range of output values of approximately 232 to 242. In this range of log compression function values, each of five contiguous and mutually exclusive ranges of input values maps to one of five discrete possibilities of output values (235, 236, 237, 238, and 239). For example, all inputs in the range indicated by the double-arrowed line segment (in red) map to an output value of 237. This range can be represented by two threshold values, such that all input values between these two threshold value (e.g., larger than the smaller threshold value among the pair of threshold values, and smaller than the larger threshold value among the pair of threshold values) map to the same output value. Hence, a log compression function reduces the number of bits needed to represent an input value (e.g. 32 bits) by mapping said input value to an output value with fewer bits (e.g. 8 bits).

After a compression function has been used to map each of one or more input values (with a number of input bits m) to a corresponding output value (with a number of output bits n), where n<m, a look-up table may store the ($2^n-1$) input threshold values (e.g., th{1}, th{2}, th{$2^n-1$}) corresponding to the $2^n$ possible output values. The first (e.g., smallest) of the possible output values may correspond to all input values less than th{1} (e.g., the first threshold value among the set of input threshold values). The second (e.g., second smallest) of the possible output values may correspond to all input values between th{1} and th{2} (e.g., greater than or equal to th{1}, and less than th{2}). In general, the $i^{th}$ (e.g., $i^{th}$ smallest) of the possible output values may correspond to all input values between th{i} and th{i+1} (e.g., greater than or equal to th{i}, and less than th{i+1}). The largest of the possible output values may correspond to all input values greater than or equal to th{$2^n-1$}. The size of the lookup table may be m·($2^n-1$). The set of threshold values may be generated using a compression function (e.g., a log compression function).

The particular number of bits may vary, depending on the particular implementations. For example, there may be 8-bit output values, in which case there could be 8 stages where each input value is compared against 8 threshold values. In some implementations, the number of output values is limited to 256 output values (e.g., 0 to 255).

As described herein, in various implementations, generation of the processed image data may be based on a predetermined table, such as table 320 (e.g., a lookup table). For example, the processed image data may be based on output values determined from table 320, where image processor 318 may determine the output values based on the input values, or dynamic subranges into which the input values fall.

In various implementations, the predetermined table includes predetermined thresholds associated with the dynamic subranges. In various implementations, the predetermined table maps input values to the output values based on the predetermined thresholds. In some implementations, each output value is associated with a unique dynamic subrange. For example, in some implementations, table 320 may store ($2^n-1$) input threshold values (e.g., th{1}, th{$2^n-1$}), where table 320 may have a size m·($2^n-1$), and where n is the number of output bits and m is the number of input bits.

The lookup table may be used to find a function output value ("output"), given an input value ("input"), as follows. If input<th{1}, the output is 0. If input is greater than or equal to th{$2^n-1$}, the output is ($2^n-1$). If input is between th{i} and th{i+1} (e.g., greater than or equal to th{i}, and less than th{i+1}), the output is i. This procedure of finding a function output value given an input value, using a lookup table, may be referred to as "performing a lookup" in a lookup table.

Figure 15:
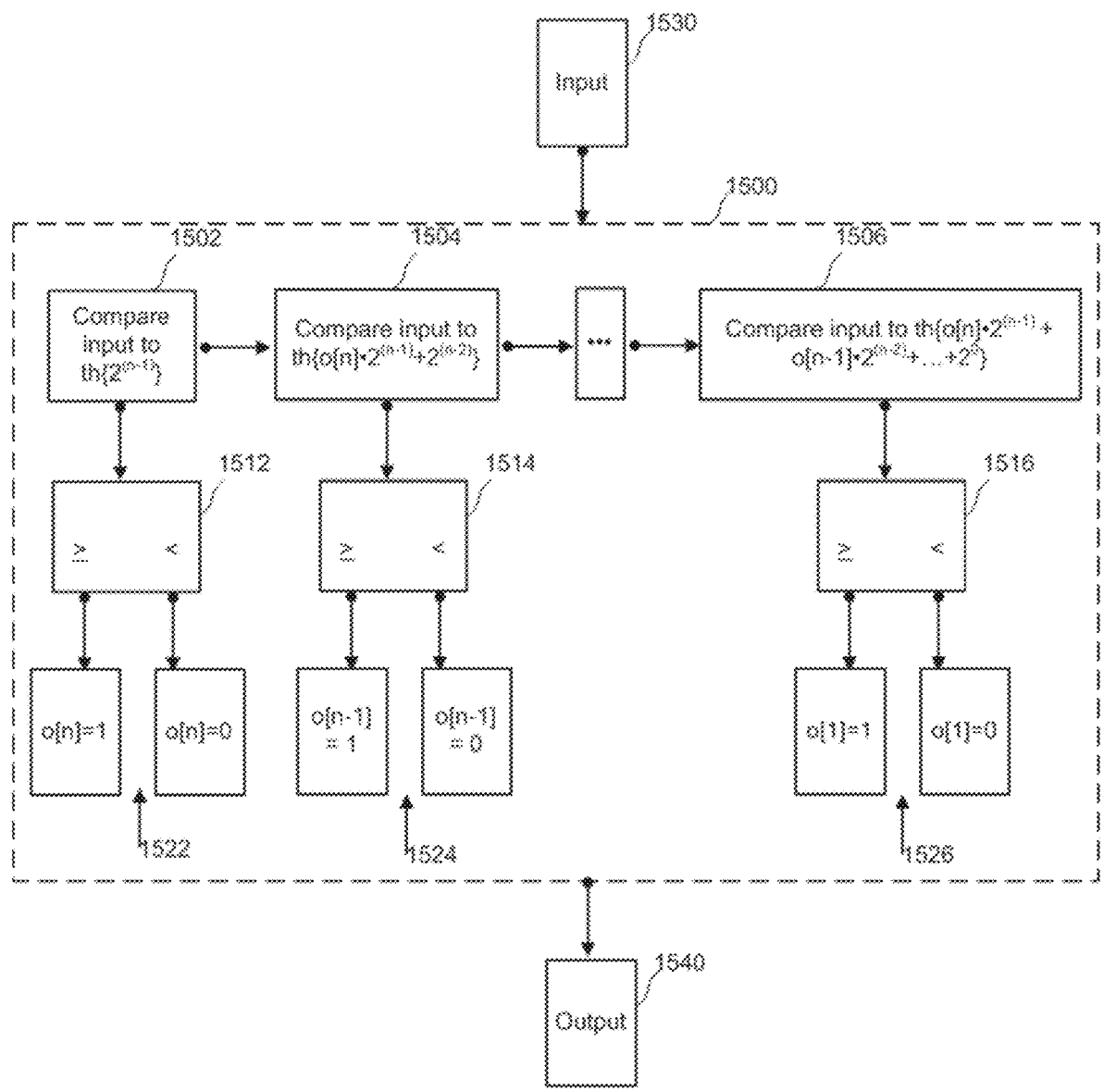
FIG. 15 illustrates a recursive binary search method to determine output values based on threshold values in a lookup table, which may be used for some embodiments described herein.

FIG. 15 illustrates a recursive binary search method to determine output values based on threshold values in a lookup table, which may be used for some embodiments described herein. This recursive binary search method may be performed by an apparatus to perform a lookup in a lookup table by generating the n bits of an output given an input. The binary search identifies a dynamic subrange for each input value, and maps the input values to the output values based on the dynamic subranges. In other words, in various implementations, multiple input values map to a single dynamic subrange, and each dynamic subrange maps to a single output value. As such, one or more of the input values are associated with a single output value. Stated differently, each output value is associated with one or more input values (or in some cases, possibly no input values). This binary search may comprise taking each input number and comparing said input number to different subdynamic range thresholds in order to determine in which subdynamic range each input number falls, where each dynamic subrange maps to a particular output value. Other types of search methods may be used to identify threshold values with a lookup table, e.g. a linear search.

As shown in FIG. 15, the recursive binary search method 1500 may be performed as follows. In each of n stages of the recursive binary search method 1500, given an input value (or "input") 1530, one bit of the n bits that comprise the output value (or "output") 1540 may be generated (e.g., beginning with the most significant bit (MSB) of the output value (o[n]) in the first stage of the n stages, and ending with the least significant bit (LSB) of the output value (o[1]) in the nth stage of the n stages (the final stage)). Each stage may comprise a comparison step and a bit assignment step.

At step 1502, in the first stage of the recursive binary search method, the input 1530 is compared to th{$2^{(n-1)}$}. At comparison step 1512, a comparison is performed (e.g., using one or more comparators) to determine whether (1) the first value is greater than or equal to the second value or (2) the first value is less than the second value. At bit assignment step 1522, the comparison of comparison step 1512 determines a first bit of the n bits to be assigned to the output value 1540. If the input 1530 is greater than or equal to th{$2^{(n-1)}$} (e.g., case (1) of comparison step 1512), the most significant bit (MSB) of the output (o[n]) is set to 1 (e.g., o[n]=1). If the input 1530 is less than th{$2^{(n-1)}$} (e.g., case (2) of comparison step 1512), the MSB of the output (o[n]) is set to 0 (e.g., o[n]=0).

At step 1504, in the second stage of the recursive binary search method, the input is compared to th{$o[n] \cdot 2^{(n-1)} + 2^{(n-2)}$}. At comparison step 1514, a comparison is performed (e.g., using one or more comparators) to determine whether (1) the first value is greater than or equal to the second value or (2) the first value is less than the second value. At bit assignment step 1524, the comparison of comparison step 1514 determines a second bit of the n bits to be assigned to the output value 1540. If the input 1530 is greater than or equal to th{$o[n] \cdot 2^{(n-1)} + 2^{(n-2)}$} (e.g., case (1) of comparison step 1514), the second MSB of the output (o[n-1]) is set to 1 (e.g., o[n-1]=1). If the input 1530 is less than th{$o[n] \cdot 2^{(n-1)} + 2^{(n-2)}$} (e.g., case (2) of comparison step 1514), the second MSB of the output (o[n-1]) is set to 0 (e.g., o[n-1]=0).

Similarly to the performing of the first two stages, in the third stage of the recursive binary search method, the input is compared to th{$o[n] \cdot 2^{(n-1)} + o[n-1] \cdot 2^{(n-2)} + 2^{(n-3)}$}. At the third comparison step, a comparison is performed (e.g., using one or more comparators) to determine whether (1) the first value is greater than or equal to the second value or (2) the first value is less than the second value. At the third bit assignment step, this comparison determines a third bit of the n bits to be assigned to the output value 1540. If the input 1530 is greater than or equal to th{$o[n] \cdot 2^{(n-1)} + o[n-1] \cdot 2^{(n-2)} + 2^{(n-3)}$}, the third MSB of the output (o[n-2]) is set to 1 (e.g., o[n-2]=1). If the input 1530 is less than th{$o[n] \cdot 2^{(n-1)} + o[n-1] \cdot 2^{(n-2)} + 2^{(n-3)}$}, the third MSB of the output (o[n-2]) is set to 0 (e.g., o[n-2]=0).

This recursive binary search method may repeat for all n stages until all n bits of the output value 1540 are calculated. At step 1506, in the nth stage of the recursive binary search method, the input is compared to th{$o[n] \cdot 2^{(n-1)} + o[n-1] \cdot 2^{(n-2)} + \ldots + 2^0$}. At comparison step 1516, a comparison is performed (e.g., using one or more comparators) to determine whether (1) the first value is greater than or equal to the second value or (2) the first value is less than the second value. At bit assignment step 1526, the comparison of comparison step 1516 determines an nth bit (e.g., the least significant bit (LSB)) of the n bits to be assigned to the output value 1540. If the input 1530 is greater than or equal to th{$o[n] \cdot 2^{(n-1)} + o[n-1] \cdot 2^{(n-2)} + \ldots + 2^0$} (e.g., case (1) of comparison step 1516), the LSB of the output (o[1]) is set to 1 (e.g., o[1]=1). If the input 1530 is less than th{$o[n] \cdot 2^{(n-1)} + o[n-1] \cdot 2^{(n-2)} + \ldots + 2^0$} (e.g., case (2) of comparison step 1516), the LSB of the output (o[1]) is set to 0 (e.g., o[0]=0). In this manner, each successive stage of the recursive binary search method may generate a successive bit of the output 1540, and performing all n stages of the recursive binary search method 1500 may generate all n bits of the output value 1540.

Although FIG. 15 shows a recursive binary search method in accordance with an embodiment, a person of ordinary skill in the art will recognize many adaptations and variations. For example, the steps can be performed in any order. Some of the steps may be removed, some of the steps can be repeated, and additional steps can be performed.

In some implementations, the stages of the binary search are performed in series and form a serialized pipeline such that the incoming stream of input values is accepted at a constant rate. In various implementations, no buffer for the incoming input values is required. Once a particular input value passes from the first stage to the second stage, the next input value may come into the first stage. Such pipelining may occur at each stage.

TABLE 2

| Stage Number | Threshold Values Needed | Concatenated Stages for Output |
|---|---|---|
| 1st | th{$2^{(n-1)}$} (th{1000 . . . 00'b}) | |
| 2nd | th{$2^{(n-2)}$} th{$2^{(n-1)} + 2^{(n-2)}$} (th{X100 . . . 00'b}) | where X is the comparator output of the first stage |
| 3rd | th{XX10 . . . 00'b} | XX is the concatenated output of the first two comparators |

TABLE 2-continued

| Stage Number | Threshold Values Needed | Concatenated Stages for Output |
|---|---|---|
| ... | ... | ... |
| nth | th{XXXX ... X1'b} | XXXX ... X is the concatenated output of all the previous comparators |

Table 2 illustrates a method to perform lookup table segmentation, which may be used for some embodiments described herein. The lookup table may be divided in n sub-tables for the n stages. For example, for an 8-bit output function, table 320 may be divided into 8 sub-tables in an 8-stage implementation. The table data needed in the individual stages of the recursive binary search method may be mutually exclusive. For example, only th$\{2^{(n-1)}\}$ is needed in the first stage, e.g. to generate the MSB of the output value (e.g., in binary, th{1000 ... 00'b}). Only th$\{2^{(n-2)}\}$ and th$\{2^{(n-1)}+2^{(n-2)}\}$ are needed in the second stage (e.g., in binary, th{X100 ... 00'b}, where X is the comparator output of the first stage). Only th{XX10 ... 00'b} are needed in the third stage, where XX is the concatenated output of the first two comparators. This reasoning can be applied to each successive stage, until only th{XXXX ... X1'b} are needed in the last stage, where XXXX ... X is the concatenated output of all the previous comparators. The address to the sub-table may be the concatenated comparator output of all the previous stages. Further, the final output of the function may be the concatenated output of all n comparators.

In various implementations, image processor 318 functions as a compression module, where the number of output values may be limited to a predetermined number of output values (e.g., 256 output values ranging from 0 to 255, etc.).

In various implementations, image processor 318 converts the input values of the raw image data to a grayscale range, where image processor 318 associates the output values with shades of gray for display. In some implementations, the input values fall within a first dynamic range, and the output values fall within a second dynamic range, which is smaller than the first dynamic range. For example, the raw image data may provide an image that includes 14 bits or 16 bits per pixel. Image processor 318 compresses the raw image data and generates an image that is 8 bits per pixel, which provides 256 different shades of gray.

Although the steps, operations, or computations may be presented in a specific order, the order may be changed in particular implementations. Other orderings of the steps are possible, depending on the particular implementation. In some particular implementations, multiple steps shown as sequential in this specification may be performed at the same time. Also, some implementations may not have all of the steps shown and/or may have other steps instead of, or in addition to, those shown herein.

Implementations described herein provide various benefits. For example, implementations provide processed image data that is high-quality and that has a small dynamic range. Implementations provide a compressed dynamic range without compromising accuracy.

Figure 16:
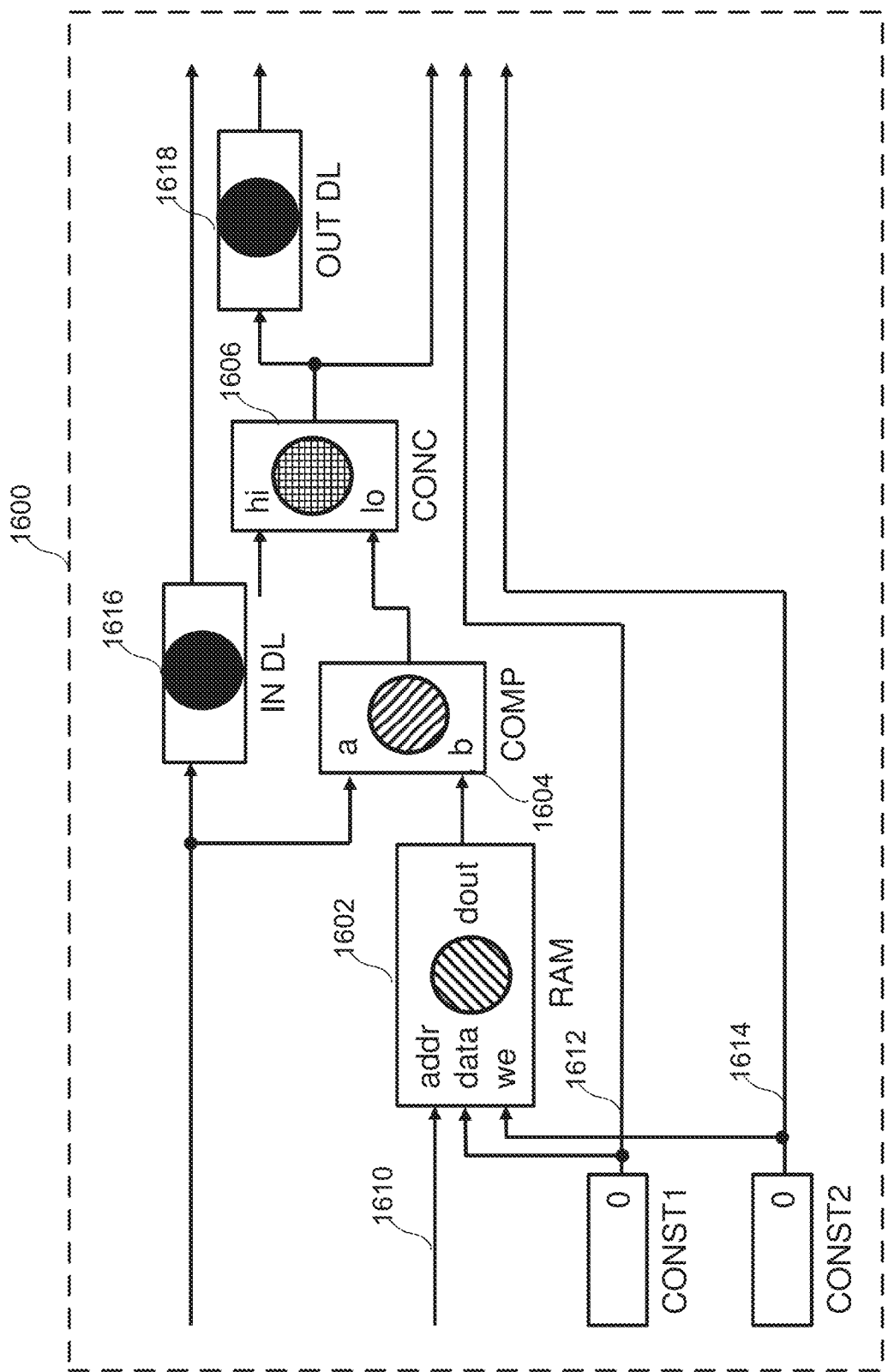
FIG. 16 illustrates a block diagram showing an example hardware implementation of one stage of a dynamic range data compression method, which may be used for some embodiments described therein.
Figure 17:
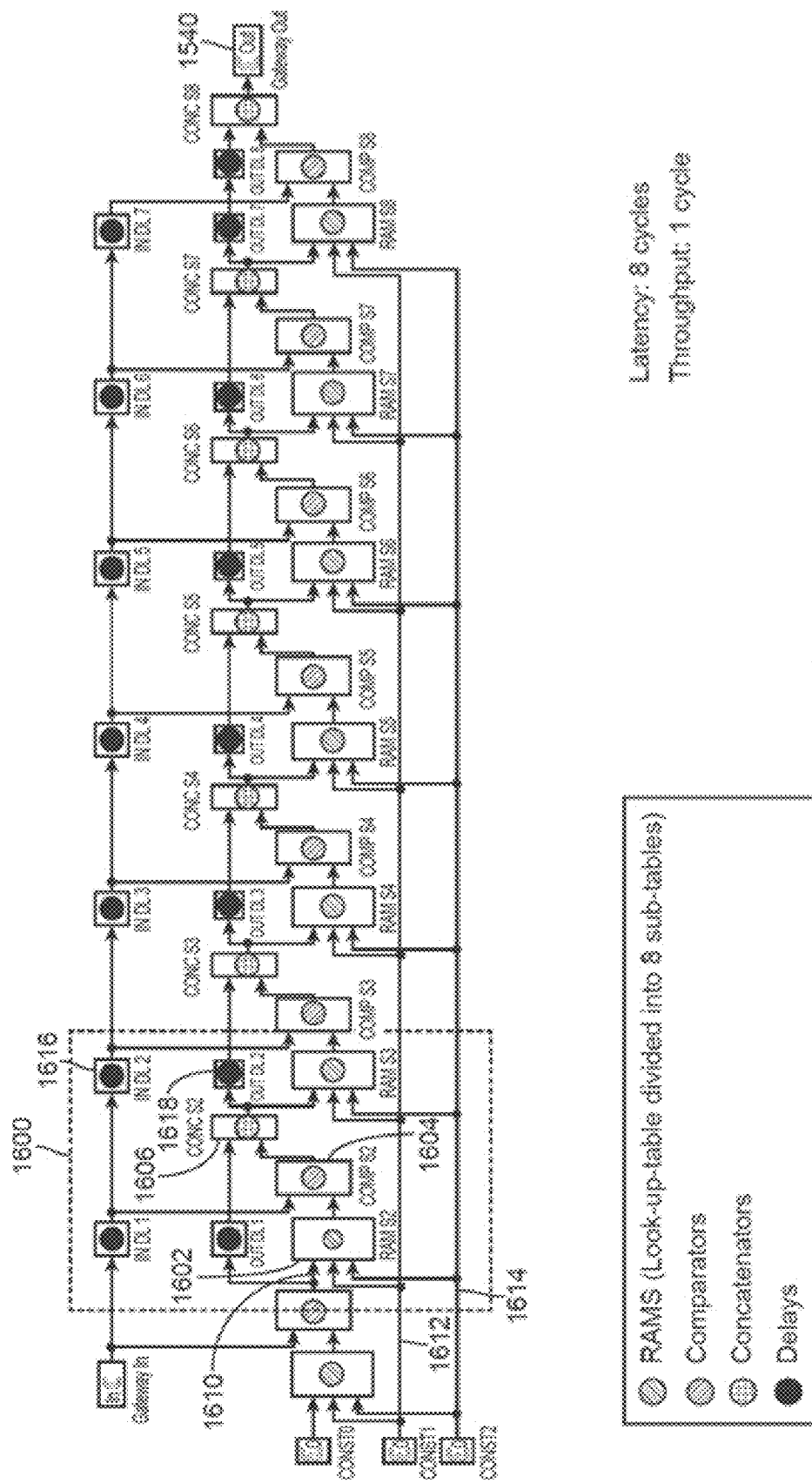
FIG. 17 illustrates a block diagram showing an example hardware implementation of an 8-stage data compression method, which may be used for some embodiments described therein.

FIG. 16 illustrates a block diagram showing an example hardware implementation of one stage of an n-stage data compression circuit, which may be used for some embodiments described therein. FIG. 17 illustrates a block diagram showing an example hardware implementation of an 8-stage data compression circuit, which may be used for some embodiments described therein. The hardware implementation shown here comprises 8 stages but in general may be configured to comprise n stages, where n may be any integer value of at least 2. Each stage 1600 of the n stages may comprise one or more RAMs 1602, one or more comparators 1604, one or more concatenators 1606, and one or more delays (e.g., an input delay 1616 and/or an output delay 1618), as described elsewhere herein.

Each RAM 1602 may have one or more inputs (e.g., ADDR (address) 1610, DATA 1612, WE (write enable) 1614, etc.) and one or more outputs (e.g. DOUT, data out). ADDR 1610 may be the input address for the RAM 1602 to read from or write to. For the first stage in the plurality of stages, ADDR 1610 may be hardcoded at 0 (e.g., by a constant value CONST0) for the first-stage RAM (e.g., S1) 1602. Alternatively or in combination, a first-stage RAM 1602 may be implemented using a simple register, as it stores only a single value. For a stage that is not the first stage in the plurality of stages, ADDR 1610 may comprise a concatenation of outputs from all the previous stages (as described elsewhere herein) for lookup into a sub-table stored in the RAM 1602. In the $i^{th}$ stage, ADDR 1610 may comprise (i−1) bits (e.g., a concatenation of outputs from all the previous (i−1) stages). ADDR 1610 may comprise no more than the number n of bits (e.g., dynamic range) corresponding to the compressed data. The compressed data may comprise a plurality of compressed pixels, which may be generated by methods as described elsewhere herein.

DATA 1612 may be the data to be written into the RAM S1 1602. DATA 1612 may be hardcoded at 0 (e.g., by a constant value CONST1) for a logic circuit that does not need to write data. DATA 1612 may be set at 0 (e.g., by a constant value CONST1) for one or more clock cycles during which the logic circuit does not need to write data. WE 1614 may be the write enable signal for the RAM 1602. WE 1614 may be hardcoded at 0 (e.g., by a constant value CONST2) for a logic circuit that does not need to write data. WE 1614 may be set at 0 (e.g., by a constant value CONST2) for one or more clock cycles during which the logic circuit does not need to write data. DOUT for a RAM 1602 may comprise a lookup table value retrieved at a given stage, e.g., during a recursive binary search method. Comparators 1604 for a given stage may generate bitwise values of a portion of output words, as described elsewhere herein. Concatenators 1606 may concatenate (e.g., join together) a bit of the output word generated at a given stage with one or more bits generated from previous stages.

A plurality of dynamic range compressed pixels may be generated from a plurality of uncompressed pixels comprising a first intensity resolution (e.g., a first dynamic range) by compressing the uncompressed pixels to be represented by a second intensity resolution (e.g., a second dynamic range less than the first dynamic range). The first dynamic range may comprise, e.g., 2 bits, 4 bits, 8 bits, 16 bits, 24 bits, 32 bits, 48 bits, 64 bits, 96 bits, 128 bits, or any number of bits in between these values. The second dynamic range may comprise a number of bits smaller than the first dynamic range (e.g., 1 bit, 2 bits, 4 bits, 8 bits, 16 bits, 24 bits, 32 bits, 48, 64 bits, 96 bits, or any number of bits in between these values). Such pixel dynamic range compression may be performed in accordance with a lookup table, as described elsewhere herein.

A data compression circuitry may be configured to generate compressed pixels at a rate sufficient to satisfy a minimum frame rate. For example, a minimum frame rate for compressed pixel generation could be 5 frames per second (fps) (e.g., 5 Hz), 10 fps (e.g., 10 Hz), 20 fps (e.g., 20 Hz), 30 fps (e.g., 30 Hz), 40 fps (e.g., 40 Hz), 50 fps (e.g., 50 Hz), 60 fps (e.g., 60 Hz), 100 fps (e.g., 100 Hz), or 200 fps (e.g., 200 Hz), in which case compressed pixels may be generated at a rate sufficient to generate a full image within a time of no more than about 200 milliseconds (ms), about 100 ms, about 50 ms, about 33 ms, about 25 ms, about 20 ms, about 17 ms, about 10 ms, or about 5 ms, respectively.

By generating a plurality of dynamic range compressed pixels at a sufficient rate (e.g., within no more than about 50 ms for a 20 Hz frame rate), a plurality of ultrasound images may be generated and subsequently outputted to a buffer of a wireless communication circuitry with a latency from a most recent acquisition time from the A/D converter to a most recent output of a compressed pixel for each of the plurality of images of no more than about 50 ms for each of the plurality of ultrasound images. Each of the plurality of ultrasound images may comprise a spatial resolution equal to the spatial resolution of uncompressed images, as well as pixels with a second intensity resolution less than the first intensity resolution of uncompressed pixels. Each of the compressed pixels may be generated at a rate of about one pixel per clock cycle of the processor, about one pixel per two clock cycles of the processor, about one pixel per three clock cycles of the processor, about one pixel per four clock cycles of the processor, or about one pixel per five cycles of the processor.

A dynamic range data compression circuitry may be configured to generate compressed pixels in a period of time no more than about 1 clock cycle, about 2 clock cycles, about 3 clock cycles, about 4 clock cycles, or about 5 clock cycles of a processor. In these cases, such a data compression circuitry may generate about 100 thousand, about 50 thousand, about 33 thousand, about 25 thousand, or about 20 thousand pixels, respectively, in a period of time corresponding to 100,000 clock cycles of a processor. Therefore, a latency between ultrasound images output may be no more than about 100,000 clock cycles, provided the ultrasound images comprise a number of pixels that can be generated at a sufficiently high rate. For example, a processor may be configured to output a plurality of compressed pixels to the buffer at a rate of at least one pixel per 0.6 microseconds (μs), which is sufficient to generate ultrasound images comprising about 58,000 pixels at a frame rate of 30 Hz.

An apparatus for compressing input words of m bits to output words of n bits, wherein n<m, may comprise a plurality of n memory components, each memory component configured to store a respective sub-table of a lookup table, wherein the lookup table comprises a plurality of ordered threshold values, the threshold values corresponding to a domain of a monotonic function and respective indices of the threshold values as ordered corresponding to a range of the monotonic function; and a logic circuit comprising bitwise operations for: determining, in a plurality of n stages respectively corresponding to the plurality of n sub-tables, based on an input word and the plurality of n sub-tables, a plurality of n bits of an output word; and concatenating the plurality of bits of to generate the output word, wherein each stage generates one bit of the output word.

Each memory component of the apparatus may be configured to store a respective sub-table of a lookup table. The memory components may be different sizes. For example, each memory component may be the smallest commonly available size (e.g., a size corresponding to a number of bits that is a power of 2) that is sufficient to fit an entire sub-table of the plurality of sub-tables that comprise a lookup table. The memory components may be the same size. For example, each memory component may be the smallest commonly available size (e.g., a size corresponding to a number of bits that is a power of 2) that is sufficient to fit the entirety of the largest sub-table of the plurality of sub-tables that comprise a lookup table.

The logic circuit may be exemplified by the block diagram shown in FIG. 16 and FIG. 17. The logic circuit may comprise one or more RAMs 1602, one or more comparators 1604, one or more concatenators 1606, and one or more delays (e.g., an input delay 1616 and/or an output delay 1618). Each RAM 1602 of the one or more RAMs may store a sub-table of a stage. Each comparator 1604 of the one or more comparators may have an output that is a bit of the final output value. Each comparator 1604 of the one or more comparators may determine a bit of an address into the RAM 1602 associated with the sub-table of a stage, as described in Table 2. Each concatenator 1606 of the one or more concatenators may concatenate the comparator output of a given stage with the concatenated bit or bits calculated and concatenated from previous stages. Each delay (e.g., an input delay 1616 and/or an output delay 1618) of the one or more delays be used for pipelining and synchronizing different data paths.

Figure 18:
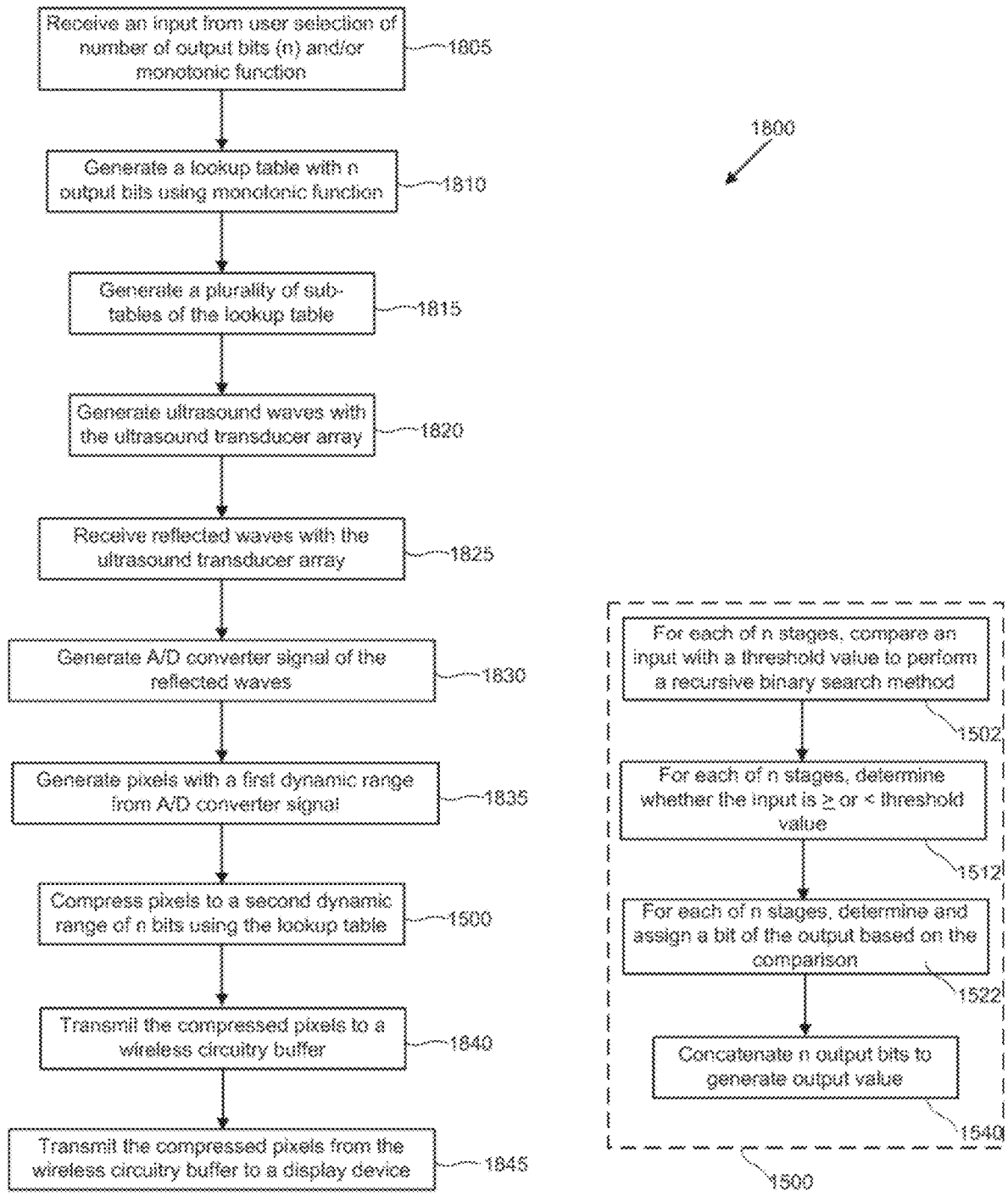
FIG. 18 illustrates a flowchart showing an example of steps to perform image compression on a handheld ultrasound probe device.

FIG. 18 illustrates a method 1800 to perform image dynamic range compression on a handheld ultrasound probe device. In step 1810, a lookup table is generated after receiving a user input of n bits (e.g., the number of output bits) and the monotonic function. Next, in step 1815, a plurality of sub-tables of the lookup table is generated. The lookup table may comprise ($2^n$–1) entries, and each data entry may comprise m bits (e.g., the number of input bits). Next, in step 1820, ultrasound waves are generated with the ultrasound transducer array. Next, in step 1825, reflected waves are received with the ultrasound transducer array. Next, in step 1830, the A/D converter generates an A/D converter signal of the reflected waves. Next, in step 1835, this A/D converter signal may be beamformed by a beamformer to generate input data (e.g., pixel data) with a first dynamic range. Next, in step 1500, the generated pixels are compressed to a second dynamic range of n bits. Next, in step 1840, the compressed pixels are transmitted to a wireless circuitry buffer. Finally, in step 1845, the compressed pixels are transmitted from the wireless circuitry buffer to a display device. In steps 1840 and/or 1845, the wireless circuitry buffer may alternatively or in combination be implemented using a wired communication connection or link.

As described elsewhere herein, step 1500 may comprise steps 1502, 1512, 1522, and 1540. In step 1502, for each of n stages, the input is compared with a threshold value to perform a recursive binary search method. Next, for each of n stages (e.g., in step 1512), the determination is made whether the input is ≥ or < the threshold value. Next, for each of n stages (e.g., in step 1522), a bit of the output is determined and assigned based on the comparison (e.g., step 1512). Finally, the n output bits are concatenated to generated the output value 1540.

Although FIG. 18 shows a method of dynamic range compression in accordance with some embodiments, a person of ordinary skill in the art will recognized many adaptations and variations. For example, the steps may be performed in any order. Some of the steps and be removed, some of the steps repeated, and additional steps performed.

The logic circuit may comprise a latency and a throughput. The apparatus may perform the plurality of n stages in n clock cycles ("cycles"). The latency of the circuit may comprise a sum of all delays (each delay corresponding to each stage) of all stages in the circuit. The latency of determining the plurality of bits of an output word may be at most n clock cycles. The latency of determining the plurality of bits of an output word may be n clock cycles. For example, an 8-stage implementation for an 8-bit output function may have a latency of 8 cycles. The cycle time (in seconds, s) may be the inverse of the frequency (in Hertz, Hz) of the processor.

The throughput of the circuit may comprise the delay time needed to calculate an output bit of a stage. The throughput of the circuit may be expressed as the rate of output words generated per clock cycle. Each stage of the plurality of stages may be performed in one clock cycle. The plurality of n stages may be configured in a pipeline to enable differently positioned bits of a plurality of output words to each be determined by a respective corresponding stage of the plurality of stages in a same clock cycle. In this way, an n-stage implementation for an n-bit output function may have a throughput of one output word per one clock cycle. A throughput of the logic circuit may be at least one output word per cycle.

An application-specific integrated circuit (ASIC) may comprise the logic circuit. A field-programmable gate array (FPGA) may comprise the logic circuit.

The apparatus may determine the plurality of n bits of the output word by performing comparisons of the input word to no more than n threshold values. This determining may be implemented by a recursive binary search method. This determining may be implemented by a search method with an expected runtime that is logarithmic order in base 2 with the number of threshold values searched, e.g., uniform binary search, Fibonacci search, exponential search, interpolation search, or fractional cascading.

The apparatus may determine the plurality of bits of the output word based on comparing the input word to a selected threshold value at each stage of the plurality of stages, the threshold value at each respective stage after the first stage being selected based on the bits of the output word determined in previous stages of the plurality of stages. For example, the recursive binary search method of FIG. 15 compares the input word to a selected threshold value at each stage of the plurality of stages. The determining of the plurality of bits of the output word may comprise: in a first stage of the plurality of stages, determining, based on a first sub-table stored in a first memory component of the plurality of memory components. This determining may be based on comparing the input word to a first threshold value stored in a first memory component of the plurality of memory components.

In each successive stage of the plurality of stages, the next most significant bit of the output word may be determined. This determining may be based on one or more corresponding additional sub-tables of the plurality of sub-tables and the most significant bit. This determining may be based on the respective sub-table stored in the corresponding memory component and bits of the output word determined in previous stages of the plurality of stages, a next bit of the output word corresponding to the respective stage. In each successive stage after the first stage of the plurality of stages, the bits of the output word may be determined based on bits determined in previous stages of the plurality of stages, which may also be used as an address of a threshold value in the memory component corresponding to the respective stage, and determining, based on comparing the input word to the threshold value at the address, a next bit of the output word corresponding to the respective stage.

Each sub-table of the lookup table of the apparatus may correspond to a respective level of a binary search tree. Each memory component may correspond to a respective level of a binary search tree. The determining of the plurality of bits of the output word may comprise searching the binary tree.

The plurality of threshold values of the apparatus may be at most $2^n-1$ threshold values. The plurality of threshold values of the apparatus may be $2^n-1$ threshold values. A size of the lookup table of the apparatus may be at most $m(2^n-1)$. A size of the lookup table of the apparatus may be $m(2^n-1)$.

The apparatus may comprise a means for dividing up the lookup table into the plurality of sub-tables. Each ith sub-table of the plurality of n sub-tables in the apparatus may comprise at most $2^{(i-1)}$ threshold values of the plurality of threshold values. Each ith sub-table of the plurality of n sub-tables in the apparatus may comprise $2^{(i-1)}$ threshold values of the plurality of threshold values.

Each ith memory component of the plurality of n memory component may be configured to store at most $m(2^{(i-1)})$ bits. Each ith memory component of the plurality of n memory component may be configured to store $m(2^{(i-1)})$ bits.

The plurality of memory components may be read-only memory (ROM). The plurality of memory components may be random-access memory (RAM).

Then bits of the apparatus may be 1, 2, 4, 8, 16, 32, 64, 128, 256, 512, 1024, or 2048 bits. The m bits of the apparatus may be 2, 4, 8, 16, 32, 64, 128, 256, 512, 1024, or 2048 bits.

The input words of the apparatus may represent an image with a first dynamic range, and the output words may represent the image with a second dynamic range less than the first dynamic range. This image may be ultrasound image data. This image may be image data generated by computed tomography (CT), magnetic resonance imaging (MRI), positron emission tomography (PET), PET-CT, single-photon emission computed tomography (SPECT), X-ray radiography, thermography, endoscopy, elastography, or other medical imaging modality.

A system for compressing medical imaging data, such as ultrasound image data, may comprise a means for receiving ultrasound image data at a bitrate corresponding to m, and the apparatus for compressing the ultrasound image data to a bitrate corresponding to n. The system may be configured to compress live ultrasound data in real time to the bitrate corresponding to n. The system may comprise a means for outputting the live ultrasound image data for display at the bitrate corresponding to n. This bitrate may be achieved by using a processor with a clock cycle sufficient to achieve a necessary throughput of data compression.

The system may comprise a means for generating the plurality of threshold values based on n and the monotonic function. The system may comprise a means for storing the plurality of threshold values in the plurality of n memory components.

The system may comprise a means for receiving a user section of n. The system may be configured to have a non-user selected value of n. The system may comprise a means for receiving a user section of the monotonic function. This monotonic function may be selected from a set of a plurality of predetermined monotonic functions. The system may be configured to have a non-user selected monotonic function.

The monotonic function of the apparatus may be configured in many ways, such as a logarithmic function. The monotonic function of the apparatus may be an exponential function. The monotonic function of the apparatus may be a gamma function (e.g., $y=x^{gamma}$, where $0<gamma<1$). The monotonic function of the apparatus may be a polynomial function (e.g., monomial or binomial). The monotonic function may be a composite function of two or more monotonic functions (e.g., a logarithmic function and a gamma function). The monotonic function may be an arithmetic combination (e.g., a sum, a weighted sum, or a product) of two or more monotonic functions.

A handheld device for real-time ultrasound imaging (or another type of medical imaging) may comprise the apparatus for compressing input words of m bits to output words of n bits, wherein n<m.

A logic circuit for compressing input words of m bits to output words of n bits, wherein n<m, may comprise bitwise operations for: determining, in a plurality of n pipeline stages respectively corresponding to a plurality of n sub-tables of a lookup table, wherein the lookup table comprises a plurality of $(2^n)-1$ ordered threshold values and each ith sub-table of the n sub-tables comprises $2^{(i-1)}$ threshold values, the threshold values corresponding to a domain of a monotonic function and respective indices of the threshold values as ordered corresponding to a range of the monotonic function, a plurality of n bits of an output word; and concatenating the plurality of bits of to generate the output word; wherein a latency of the logic circuit is at most n clock cycles and a throughput of the logic circuit is at least one output word per cycle.

An application-specific integrated circuit (ASIC) may comprise the logic circuit. A field-programmable gate array (FPGA) may comprise the logic circuit. An apparatus for compressing input words of m bits to output words of n bits, wherein n<m, may comprise the logic circuit and a plurality of n discrete memory components respectively corresponding to the n pipeline stages and n sub-tables, each memory component comprising at least a minimum size necessary to store the corresponding sub-table of the plurality of n sub-tables.

Although the description has been described with respect to particular embodiments thereof, these particular embodiments are merely illustrative, and not restrictive. Concepts illustrated in the examples may be applied to other examples and implementations.

In various implementations, software is encoded in one or more non-transitory computer-readable media for execution by one or more processors. The software when executed by one or more processors is operable to perform the implementations described herein and other functions.

Any suitable programming language can be used to implement the routines of particular embodiments including C, C++, Java, assembly language, etc. Different programming techniques can be employed such as procedural or object oriented. The routines can execute on a single processing device or multiple processors. Although the steps, operations, or computations may be presented in a specific order, this order may be changed in different particular embodiments. In some particular embodiments, multiple steps shown as sequential in this specification can be performed at the same time.

Particular embodiments may be implemented in a non-transitory computer-readable storage medium (also referred to as a machine-readable storage medium) for use by or in connection with the instruction execution system, apparatus, or device. Particular embodiments can be implemented in the form of control logic in software or hardware or a combination of both. The control logic when executed by one or more processors is operable to perform the implementations described herein and other functions. For example, a tangible medium such as a hardware storage device can be used to store the control logic, which can include executable instructions.

Particular embodiments may be implemented by using a programmable general purpose digital computer, and/or by using application specific integrated circuits, programmable logic devices, field programmable gate arrays, optical, chemical, biological, quantum or nanoengineered systems, components and mechanisms. In general, the functions of particular embodiments can be achieved by any means as is known in the art. Distributed, networked systems, components, and/or circuits can be used. Communication, or transfer, of data may be wired, wireless, a combination thereof, or by any other means.

A "processor" may include any suitable hardware and/or software system, mechanism or component that processes data, signals or other information. A processor may include a system with a general-purpose central processing unit, multiple processing units, dedicated circuitry for achieving functionality, or other systems. Processing need not be limited to a geographic location, or have temporal limitations. For example, a processor may perform its functions in "real time," "offline," in a "batch mode," etc. Portions of processing may be performed at different times and at different locations, by different (or the same) processing systems. A computer may be any processor in communication with a memory. The memory may be any suitable data storage, memory and/or non-transitory computer-readable storage medium, including electronic storage devices such as random-access memory (RAM), read-only memory (ROM), magnetic storage device (hard disk drive or the like), flash, optical storage device (CD, DVD, or the like), magnetic or optical disk, or other tangible media suitable for storing instructions (e.g., program or software instructions) for execution by the processor. For example, a tangible medium such as a hardware storage device can be used to store the control logic, which can include executable instructions. The instructions can also be contained in, and provided as, an electronic signal, for example in the form of software as a service (SaaS) delivered from a server (e.g., a distributed system and/or a cloud computing system).

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope to implement a program or code that can be stored in a machine-readable medium to permit a computer to perform any of the methods described above.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A handheld ultrasound probe for generating an ultrasound image, comprising:
   an ultrasound transducer array configured to generate ultrasound data;
   a processor coupled to the ultrasound transducer array, the processor configured with instructions that when executed cause the processor to:
   receive ultrasound signals derived from the ultrasound data,
   generate radio frequency (RF) signals based on the ultrasound signals;
   generate RF samples based on the RF signals;
   generate a flag table at least in part by associating a flag with an RF
   sample of the RF samples, wherein the flag indicates whether or not the
   RF sample is used to generate the ultrasound image;
   select a subset of the ultrasound signals in accordance with & the flag table,
   generate a plurality of uncompressed pixels from the selected subset of the ultrasound signals,
   compress the plurality of uncompressed pixels to generate a plurality of compressed pixels, wherein compressing the plurality of uncompressed pixels comprises implementing a function to transform an input value of an uncompressed pixel from an ultrasound signal to a reduced-dynamic range output value for a compressed pixel from the ultrasound signal; and
   generate the ultrasound image from the plurality of compressed pixels.

2. The handheld ultrasound probe of claim 1, further comprising a wireless communication circuitry coupled to the processor, wherein the wireless communication circuitry is configured to transmit the ultrasound image.

3. The handheld ultrasound probe of claim 2, further comprising an analog-to-digital (A/D) converter configured to generate the ultrasound signals derived from the ultrasound data.

4. The handheld ultrasound probe of claim 3, further comprising:
   an energy storage configured to provide power to the ultrasound transducer array, the A/D converter, the wireless communication circuitry, and the processor; and
   a housing to support the ultrasound transducer array, the energy storage device, the A/D converter, the wireless communication circuitry, and the processor when the housing is grasped by a user.

5. The handheld ultrasound probe of claim 4, wherein the handheld ultrasound probe comprises a weight of no more than about 300 grams.

6. The handheld ultrasound probe of claim 3, wherein the processor is configured with instructions that when executed cause the processor to further output a plurality of ultrasound images to the wireless communication circuitry with a latency between compressed pixels for each of the plurality of ultrasound images of no more than about 50 milliseconds.

7. The handheld ultrasound probe of claim 6, wherein the latency between the compressed pixels is no more than about 50 clock cycles of the processor.

8. The handheld ultrasound probe of claim 3, wherein the processor is configured with instructions that when executed cause the processor to further output a plurality of ultrasound images to the wireless communication circuitry at a frame rate of at least 30 frames per second.

9. The handheld ultrasound probe of claim 2, further comprising an application specific integrated circuit (ASIC), the ASIC comprising the wireless communication circuitry and the processor.

10. The handheld ultrasound probe of claim 1, further comprising a field programming gate array (FPGA), the FPGA comprising the processor.

11. The handheld ultrasound probe of claim 1, wherein the processor comprises a receive (Rx) beamformer, the receive (Rx) beamformer using no more than about 100 milliwatts (mW) of power when generating a plurality of ultrasound images, and wherein the handheld ultrasound probe uses no more than about 15 watts (W) of power when generating the plurality of ultrasound images.

12. The handheld ultrasound probe of claim 1, wherein the flag table is compressed.

13. The handheld ultrasound probe of claim 12, wherein the processor is configured with instructions that when executed cause the processor to further decode the compressed flag table.

14. A method for generating an ultrasound image with a handheld ultrasound probe, the method comprising:
   generating ultrasound data with an ultrasound transducer array;
   receiving, by a processor, ultrasound signals derived from the ultrasound data;
   generating radio frequency (RF) signals based on the ultrasound signals;
   generating RF samples based on the RF signals;
   generating a flag table at least in part by associating a flag with an RF sample of the RF
   samples, wherein the flag indicates whether or not the RF sample is used to generate the
   ultrasound image;
   selecting, by the processor, a subset of the ultrasound signals in accordance with & the flag table;
   generating, by the processor, a plurality of uncompressed pixels from the selected subset of the ultrasound signals;
   compressing, by the processor, the plurality of uncompressed pixels to generate a plurality of compressed pixels, wherein compressing the plurality of uncompressed pixels comprises implementing a function to transform an input value of an uncompressed pixel from an ultrasound signal to a reduced-dynamic range output value for a compressed pixel from the ultrasound signal; and
   generating, by the processor, the ultrasound image from the plurality of compressed pixels.

15. The method of claim 14, further comprising transmitting the ultrasound image using a wireless communication circuitry.

16. The method of claim 15, further comprising providing, by an energy storage, power to the ultrasound transducer array, the wireless communication circuitry, and the processor, and using a housing to support the ultrasound transducer array, the energy storage device, the wireless communication circuitry, and the processor when the housing is grasped by a user.

17. The method of claim 15, further comprising outputting, by the processor, a plurality of ultrasound images to the wireless communication circuitry with a latency between compressed pixels for each of the plurality of ultrasound images of no more than about 50 milliseconds.

18. The method of claim 17, wherein the latency between the compressed pixels is no more than about 50 clock cycles of the processor.

19. The method of claim 15, further comprising outputting, by the processor, a plurality of ultrasound images to the wireless communication circuitry at a frame rate of at least 30 frames per second.

20. The method of claim 14, wherein the processor comprises a receive (Rx) beamformer, the receive (Rx) beamformer using no more than about 100 milliwatts (mW) of power when generating a plurality of ultrasound images, and wherein the handheld ultrasound probe uses no more than about 15 watts (W) of power when generating the plurality of ultrasound images.

21. The method of claim 14, wherein the flag table is compressed.

22. The method of claim 21, further comprising decoding the compressed flag table.

23. The method of claim 14, further comprising using an analog-to-digital (A/D) converter to generate the ultrasound signals derived from the ultrasound data.

24. A handheld ultrasound probe for generating an ultrasound image, comprising:
an ultrasound transducer array configured to generate ultrasound data;
a processor coupled to the ultrasound transducer array, the processor configured with instructions that when executed cause the processor to:
receive ultrasound signals derived from the ultrasound data,
generate radio frequency (RF) signals based on the ultrasound signals;
generate RF samples based on the RF signals;
generate a compressed flag table at least in part by:
generating a flag table at least in part by associating a flag with an RF sample of the RF samples, wherein the flag indicates whether or not the RF sample is used to generate the ultrasound image;
identifying a pattern of flag values within the flag table;
reducing the information in the flag table in accordance with the pattern; and
storing records of flag values that deviate from the pattern;
select a subset of the ultrasound signals in accordance with the compressed flag table,
generate a plurality of uncompressed pixels from the selected subset of the ultrasound signals,
compress the plurality of uncompressed pixels to generate a plurality of compressed pixels, wherein compressing the plurality of uncompressed pixels comprises implementing a function to transform an input value of an uncompressed pixel from an ultrasound signal to a reduced-dynamic range output value for an compressed pixel from the ultrasound signal; and
generate the ultrasound image from the plurality of compressed pixels.

* * * * *